(12) United States Patent
Robinson et al.

(10) Patent No.: US 11,364,021 B2
(45) Date of Patent: Jun. 21, 2022

(54) BIOPSY DEVICE WITH STERILE SLEEVE

(71) Applicant: Devicor Medical Products, Inc., Cincinnati, OH (US)

(72) Inventors: Andrew Robinson, Cincinnati, OH (US); Andrew Paul Nock, Dayton, OH (US); Edward A. Rhad, Fairfield, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 349 days.

(21) Appl. No.: 16/567,244

(22) Filed: Sep. 11, 2019

(65) Prior Publication Data

US 2020/0000444 A1 Jan. 2, 2020

Related U.S. Application Data

(63) Continuation of application No. 16/117,405, filed on Aug. 30, 2018, now Pat. No. 10,448,932, which is a
(Continued)

(51) Int. Cl.
*A61B 5/00* (2006.01)
*A61B 10/02* (2006.01)
(Continued)

(52) U.S. Cl.
CPC ...... *A61B 10/0233* (2013.01); *A61B 10/0275* (2013.01); *A61B 46/10* (2016.02);
(Continued)

(58) Field of Classification Search
CPC . A61B 10/0233; A61B 10/0275; A61B 46/10; A61B 46/17; A61B 2010/0208;
(Continued)

(56) References Cited

U.S. PATENT DOCUMENTS 3,913,566 A 10/1975 Lacey
4,878,485 A 11/1989 Adair
(Continued)

FOREIGN PATENT DOCUMENTS

CN 104518351 A 4/2015
WO WO 2017/046531 A1 3/2017

OTHER PUBLICATIONS

Hahn, Markus et al., "Vacuum Assisted Breast Biopsy with Mammotome®," available Nov. 11, 2012, copyright 2013 by Devicor Medical Germany GmbH, published in Germany by Springer Medizin Verlag. 128 pages.
(Continued)

*Primary Examiner* — May A Abouelela
(74) *Attorney, Agent, or Firm* — Frost Brown Todd LLC

(57) ABSTRACT

A sterile cover assembly is for a biopsy device. The biopsy device includes a reusable holster including a housing and driving mechanism. The driving mechanism is for driving a cutter in a needle of a probe. The housing is adapted to releasably couple to the probe. The sterile cover assembly includes a sleeve and a flexible sterile cover. The sleeve is configured to receive at least a portion of the housing of the reusable holster. The sterile cover is coupled to the sleeve and is configured to cover the housing of the holster.

17 Claims, 11 Drawing Sheets

Related U.S. Application Data continuation of application No. 15/977,797, filed on May 11, 2018, now Pat. No. 10,335,125.

(60) Provisional application No. 62/505,571, filed on May 12, 2017.

(51) Int. Cl.
*A61B 46/10* (2016.01)
*A61B 46/17* (2016.01)
*A61B 17/00* (2006.01)

(52) U.S. Cl.
CPC ...... *A61B 46/17* (2016.02); *A61B 2010/0208* (2013.01); *A61B 2017/00477* (2013.01); *A61B 2560/0456* (2013.01)

(58) Field of Classification Search
CPC .. A61B 2017/00477; A61B 2560/0456; A61B 50/00; A61B 2050/0065
USPC ......................... 600/437, 562, 567
See application file for complete search history.

(56) References Cited

U.S. PATENT DOCUMENTS

| | | | | |
|---|---|---|---|---|
| 4,892,521 A | * | 1/1990 | Laico | A61M 5/3243 604/192 |
| 5,015,240 A | * | 5/1991 | Soprani | A61M 5/326 604/192 |
| 5,259,383 A | * | 11/1993 | Holstein | A61B 8/4281 600/437 |
| 5,413,573 A | | 5/1995 | Koivukangas | |
| 5,433,221 A | * | 7/1995 | Adair | A61B 46/10 128/849 |
| 5,469,863 A | * | 11/1995 | Shah | A41D 19/0068 128/844 |
| 5,526,822 A | | 6/1996 | Burbank et al. | |
| 5,605,009 A | * | 2/1997 | Elder | A01G 13/0281 47/32 |
| 5,795,632 A | * | 8/1998 | Buchalter | A61B 8/12 206/305 |
| 5,910,113 A | * | 6/1999 | Pruter | A61B 8/12 600/437 |
| 5,928,164 A | | 7/1999 | Burbank et al. | |
| 5,997,481 A | * | 12/1999 | Adams | A61B 8/4281 600/459 |
| 6,000,400 A | * | 12/1999 | Navis | A61B 46/10 128/849 |
| 6,017,316 A | | 1/2000 | Ritchart et al. | |
| 6,051,293 A | * | 4/2000 | Weilandt | G01K 13/25 428/35.2 |
| 6,059,759 A | * | 5/2000 | Mottola | A61M 25/00 604/264 |
| 6,086,544 A | | 7/2000 | Hibner et al. | |
| 6,162,187 A | | 12/2000 | Buzzard et al. | |
| 6,267,726 B1 | * | 7/2001 | Grimm | A61B 1/00142 600/459 |
| 6,432,065 B1 | | 8/2002 | Burdorff et al. | |
| 6,443,910 B1 | * | 9/2002 | Krueger | A61B 10/025 600/567 |
| 6,530,933 B1 | * | 3/2003 | Yeung | A61B 17/0401 128/898 |
| 6,626,849 B2 | | 9/2003 | Huitema et al. | |
| 6,752,768 B2 | | 6/2004 | Burdorff et al. | |
| 7,037,275 B1 | * | 5/2006 | Marshall | A61B 10/02 600/562 |
| 7,442,171 B2 | | 10/2008 | Stephens et al. | |
| 7,648,466 B2 | | 1/2010 | Stephens et al. | |
| 7,837,632 B2 | | 11/2010 | Stephens et al. | |
| 7,850,620 B2 | * | 12/2010 | Miller | A61B 46/10 600/568 |
| 7,850,664 B1 | * | 12/2010 | Pruter | A61B 46/10 604/263 |
| 7,854,706 B2 | | 12/2010 | Hibner | |
| 7,914,464 B2 | | 3/2011 | Burdorff et al. | |
| 7,938,786 B2 | | 5/2011 | Ritchie et al. | |
| 8,083,687 B2 | | 12/2011 | Parihar | |
| 8,118,743 B2 | * | 2/2012 | Park | A61B 8/4422 600/437 |
| 8,118,755 B2 | | 2/2012 | Hibner et al. | |
| 8,182,493 B2 | * | 5/2012 | Cole | A61B 17/3468 606/131 |
| 8,206,316 B2 | | 6/2012 | Hibner et al. | |
| 8,241,226 B2 | | 8/2012 | Hibner et al. | |
| 8,398,540 B2 | | 3/2013 | Hassidov et al. | |
| 8,454,531 B2 | | 6/2013 | Speeg et al. | |
| 8,532,747 B2 | | 9/2013 | Nock et al. | |
| 8,622,924 B2 | | 1/2014 | Speeg et al. | |
| 8,702,623 B2 | | 4/2014 | Parihar et al. | |
| 8,764,680 B2 | | 7/2014 | Rhad et al. | |
| 8,795,183 B2 | * | 8/2014 | Siebrecht | A61B 17/320068 600/459 |
| 8,801,742 B2 | | 8/2014 | Rhad et al. | |
| 8,858,465 B2 | | 10/2014 | Fiebig | |
| 8,938,285 B2 | | 1/2015 | Fiebig et al. | |
| 8,944,069 B2 | * | 2/2015 | Miller | A61B 50/3001 128/852 |
| 9,072,543 B2 | * | 7/2015 | Miller | A61B 50/20 |
| 9,095,326 B2 | | 8/2015 | Ritchie et al. | |
| 9,326,755 B2 | | 5/2016 | Fiebig et al. | |
| 9,345,457 B2 | | 5/2016 | Speeg et al. | |
| 9,427,254 B2 | | 8/2016 | Murphy | |
| 9,486,186 B2 | | 11/2016 | Fiebig et al. | |
| 9,724,076 B2 | | 8/2017 | Fiebig et al. | |
| 9,820,722 B1 | * | 11/2017 | Malanowska-Stega | A61B 10/0291 |
| 9,877,706 B2 | | 1/2018 | Speeg et al. | |
| 10,335,125 B2 | | 7/2019 | Robinson et al. | |
| 10,368,951 B2 | | 8/2019 | Moll et al. | |
| 10,398,415 B2 | | 9/2019 | Nock et al. | |
| 10,405,937 B2 | | 9/2019 | Black et al. | |
| 10,413,280 B2 | | 9/2019 | Speeg et al. | |
| 10,488,932 B1 | | 11/2019 | Keller et al. | |
| 10,799,211 B2 | * | 10/2020 | Nordgren | A61B 8/4422 |
| 2002/0087047 A1 | | 7/2002 | Remijan et al. | |
| 2002/0115942 A1 | * | 8/2002 | Stanford | A61F 2/01 600/562 |
| 2003/0149366 A1 | * | 8/2003 | Stringer | A61B 8/42 600/464 |
| 2006/0074345 A1 | | 4/2006 | Hibner | |
| 2006/0264751 A1 | * | 11/2006 | Wendelken | A61B 8/4281 600/439 |
| 2007/0239082 A1 | * | 10/2007 | Schultheiss | A61B 46/17 601/4 |
| 2007/0270775 A1 | * | 11/2007 | Miller | A61B 10/025 604/506 |
| 2009/0131821 A1 | | 5/2009 | Speeg et al. | |
| 2009/0155341 A1 | * | 6/2009 | Gavriely | A61L 31/16 424/445 |
| 2010/0152610 A1 | | 6/2010 | Parihar et al. | |
| 2010/0160819 A1 | | 6/2010 | Parihar et al. | |
| 2013/0324882 A1 | | 12/2013 | Mescher et al. | |
| 2014/0053461 A1 | * | 2/2014 | Blaha | A01G 13/00 47/20.1 |
| 2014/0262880 A1 | | 9/2014 | Yoon | |
| 2015/0094611 A1 | * | 4/2015 | Farhadi | A61B 10/04 600/562 |
| 2016/0192903 A1 | * | 7/2016 | Nordgren | A61B 8/4422 600/437 |
| 2016/0228188 A1 | * | 8/2016 | Sweeney | A61B 17/3494 |
| 2016/0278738 A1 | * | 9/2016 | Buchalter | A61B 8/42 |
| 2017/0281143 A1 | * | 10/2017 | Laub | A61B 17/00234 |
| 2018/0116746 A1 | * | 5/2018 | Lennertz | A61B 46/23 |
| 2018/0153529 A1 | | 6/2018 | Nock et al. | |

(56) References Cited

U.S. PATENT DOCUMENTS

2018/0310911 A1* 11/2018 Nix .................. A61B 46/17
2019/0110779 A1* 4/2019 Gardner ............ A61B 10/02

OTHER PUBLICATIONS

Chinese Office Action dated Jul. 27, 2020 for Application No. 201880030048.3, 8 pages.
Chinese Office Action dated Mar. 21, 2021 for Application No. 201880030048.3, 18 pages.
Chinese Office Action dated Jul. 7, 2021 for Application No. 201880030048.3, 6 pages.
European Communication dated Sep. 10, 2020 for Application No. 18729233.9, 6 pages.
European Communication dated Jan. 29, 2021 for Application No. 18729233.9, 6 pages.
European Communication dated Jun. 9, 2021 for Application No. 18729233.9, 5 pages.
International Search Report and Written Opinion dated Aug. 13, 2018 for Application No. PCT/US2018/032390, 12 pgs.
U.S. Appl. No. 61/566,793, filed Dec. 5. 2011.

* cited by examiner

BIOPSY DEVICE WITH STERILE SLEEVE

BACKGROUND

This application is a continuation of U.S. application Ser. No. 16/117,405, entitled "Biopsy Device with Sterile Sleeve," filed Aug. 30, 2018, which is a continuation of U.S. application Ser. No. 15/977,797, entitled "Biopsy Device with Sterile Sleeve," filed May 11, 2018, which claims priority to U.S. Provisional Patent App. No. 62/505,571, entitled "Biopsy Device with Sterile Sleeve," filed May 12, 2017, the disclosure disclosures of which are incorporated by reference herein.

BACKGROUND

A biopsy is the removal of a tissue sample from a patient to enable examination of the tissue for signs of cancer or other disorders. Tissue samples may be obtained in a variety of ways using various medical procedures involving a variety of the sample collection devices. For example, biopsies may be open procedures (surgically removing tissue after creating an incision) or percutaneous procedures (e.g. by fine needle aspiration, core needle biopsy, or vacuum assisted biopsy). After the tissue sample is collected, the tissue sample may be analyzed at a lab (e.g. a pathology lab, biomedical lab, etc.) that is set up to perform the appropriate tests (such as histological).

Biopsy samples have been obtained in a variety of ways in various medical procedures including open and percutaneous methods using a variety of devices. For instance, some biopsy devices may be fully operable by an operator using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

The state of the art for breast biopsy is vacuum-assisted breast biopsy. A current textbook in this area is "Vacuum-Assisted Breast Biopsy with Mammotome®" available Nov. 11, 2012, copyright 2013 by Devicor Medical Germany GmBh, published in Germany by Springer Medizin Verlag, Authors: Markus Hahn, Anne Tardivon and Jan Casselman, ISBN 978-3-642-34270-7.

Biopsy devices may be used under ultrasound image guidance, stereotactic (X-ray) guidance, Mill guidance, Positron Emission Mammography ("PEM" guidance), Breast-Specific Gamma Imaging ("BSGI") guidance, or otherwise. Each procedure has its own methodology based on the form of imaging guidance used.

Known biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 7,442,171, entitled "Remote Thumbwheel for a Surgical Biopsy Device," issued Oct. 8, 2008; U.S. Pat. No. 7,938,786, entitled "Vacuum Timing Algorithm for Biopsy Device," issued May 10, 2011; U.S. Pat. No. 8,118,755, entitled "Biopsy Sample Storage," issued Feb. 1, 2012; U.S. Pat. No. 8,532,747, entitled "Biopsy Marker Delivery Device," issued Sep. 10, 2013; U.S. Pat. No. 8,764,680, entitled "Handheld Biopsy Device with Needle Firing," issued on Jun. 11, 2014; U.S. Pat. No. 8,858,465, entitled "Biopsy Device with Motorized Needle Firing," issued Oct. 14, 2014; U.S. Pat. No. 9,326,755, entitled "Biopsy Device Tissue Sample Holder with Bulk Chamber and Pathology Chamber," issued May 3, 2016; and U.S. Pat. No. 9,486,186, entitled "Biopsy Device With Slide-In Probe," issued Nov. 8, 2016. The disclosure of each of the above-cited U.S. Patents is incorporated by reference herein.

Additionally known biopsy devices and biopsy system components are disclosed in U.S. Pub. No. 2006/0074345, entitled "Biopsy Apparatus and Method," published Apr. 6, 2006 and now abandoned; U.S. Pub. No. 2010/0152610, entitled "Hand Actuated Tetherless Biopsy Device with Pistol Grip," published Jun. 17, 2010, now abandoned; U.S. Pub. No. 2010/0160819, entitled "Biopsy Device with Central Thumbwheel," published Jun. 24, 2010, now abandoned; and U.S. Pub. No. 2013/0324882, entitled "Control for Biopsy Device," published Dec. 5, 2013. The disclosure of each of the above-cited U.S. Patent Application Publications is incorporated by reference herein.

U.S. Pub. No. 2014/0275999, entitled "Biopsy device" published Sep. 18, 2014, and U.S. Pub. No. 2016/0183928, entitled "Biopsy Device," published Jun. 30, 2016, both describe some aspect of a biopsy device including a probe, a holster, and a tissue sample holder for collecting tissue samples. The probe includes a needle and a hollow cutter. The tissue sample holder includes a housing having a plurality of chambers that are configured to receive a plurality of strips connected by at least one flexible member. The flexible member is configured to permit the strips to pivot relative to each other such that the strips can shift between a flat configuration and an arcuate configuration. The tissue sample holder is rotatable to successively index each chamber to the cutter lumen such that tissue samples may be collected in the strips. The strips may be removed from the tissue sample holder and placed in a tissue sample holder container for imaging of tissue samples.

While several systems and methods have been made and used for obtaining and processing a biopsy sample, it is believed that no one prior to the inventor has made or used the invention described in the appended claims.

BRIEF DESCRIPTION OF THE DRAWINGS

It is believed the present invention will be better understood from the following description of certain examples taken in conjunction with the accompanying drawings, in which like reference numerals identify the same elements and in which.

Figure 1:
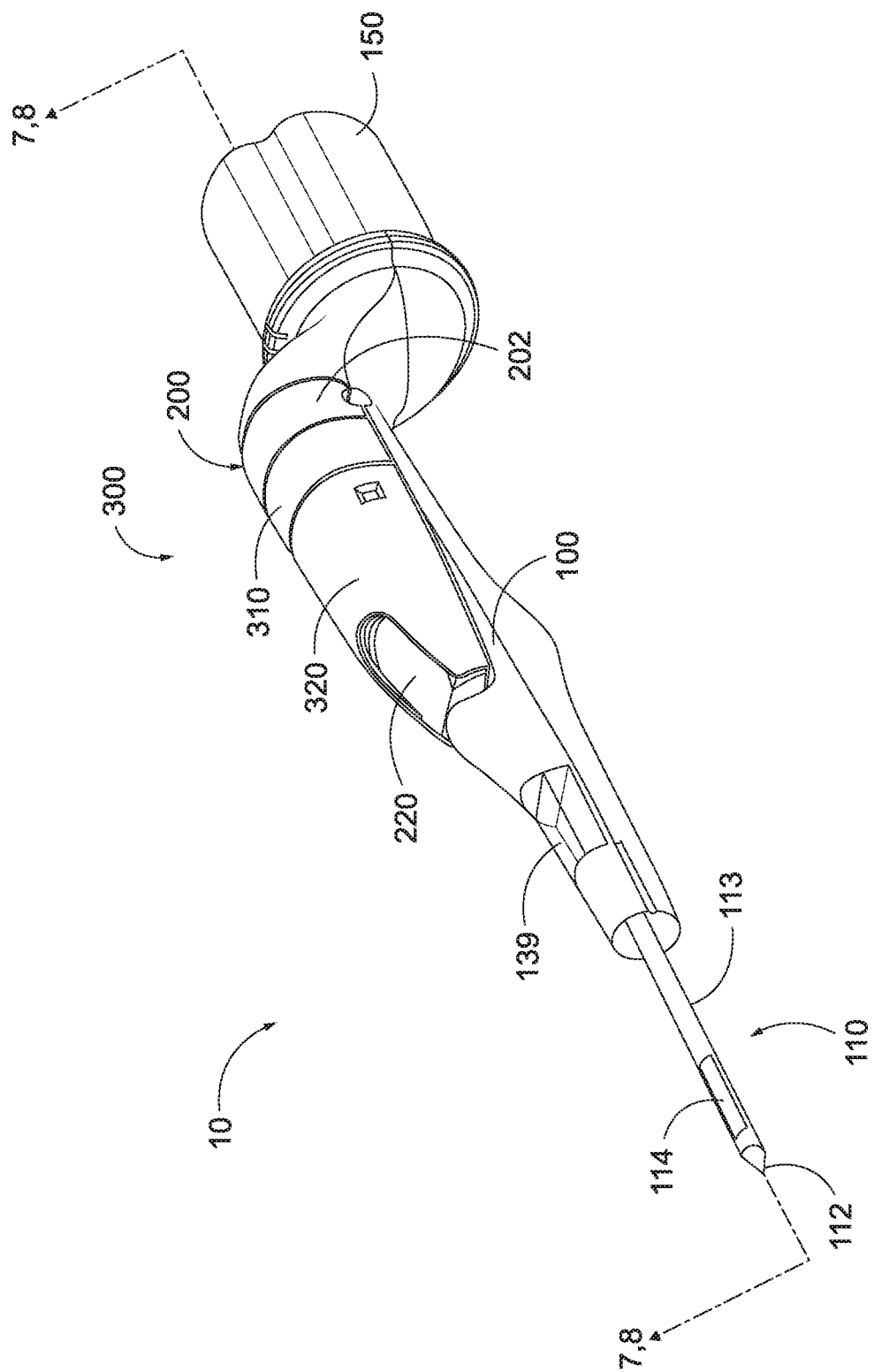
FIG. 1 depicts a perspective view of an exemplary biopsy device including an exemplary removable cover assembly coupled to a portion of the biopsy device.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION OF THE INVENTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Exemplary Biopsy Device

FIG. 1 shows an exemplary biopsy device (10) that may be used in a breast biopsy system. Biopsy device (10) of the present examples comprises a probe (100) and a holster (200). A needle (110) extends distally from probe (100) and is inserted into a patient's tissue to obtain tissue samples. These tissue samples are deposited in a tissue sample holder (150) at the proximal end of probe (100).

Holster (200) of the present example is selectively attachable to probe (100) to provide actuation of various components within probe (100). In the present configuration, holster (200) is a reusable component, while probe (100) and tissue sample holder (150) are disposable. It should be understood that the use of the term "holster" herein should not be read as requiring any portion of probe (100) to be inserted into any portion of holster (200). For instance, in the present example, holster (200) may include a retention feature (240) that is received by probe (100) to releasably secure probe (100) to holster (200). Probe (100) also includes a set of resilient tabs (not shown) or other suitable release features that may be pressed inwardly to disengage retention feature (240), such that an operator may simultaneously depress both of the tabs then pull probe (100) rearwardly and away from holster (200) to decouple probe (100) from holster (200). Of course, a variety of other types of structures, components, features, etc. (e.g., bayonet mounts, latches, clamps, clips, snap fittings, etc.) may be used to provide removable coupling of probe (100) and holster (200). Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Some variations of biopsy device (10) may include one or more sensors (not shown), in probe (100) and/or in holster (200), that is/are configured to detect when probe (100) is coupled with holster (200). Such sensors or other features may further be configured to permit only certain types of probes (100) and holsters (200) to be coupled together. In addition or in the alternative, such sensors may be configured to disable one or more functions of probes (100) and/or holsters (200) until a suitable probe (100) and holster (200) are coupled together. In one merely illustrative example, probe (100) includes a magnet (not shown) that is detected by a Hall effect sensor (not shown) or some other type of sensor in holster (200) when probe (100) is coupled with holster (200). As yet another merely illustrative example, coupling of probe (100) with holster (200) may be detected using physical contact between conductive surfaces or electrodes, using RFID technology, and/or in numerous other ways as will be apparent to those of ordinary skill in the art in view of the teachings herein. Of course, such sensors and features may be varied or omitted as desired.

Biopsy device (10) of the present example is configured for handheld use and be used under ultrasonic guidance. Of course, biopsy device (10) may instead be used under stereotactic guidance, MRI guidance, PEM guidance, BSGI guidance, or otherwise. It should also be understood that biopsy device (10) may be sized and configured such that biopsy device (10) may be operated by a single hand of an operator. In particular, an operator may grasp biopsy device (10), insert needle (110) into a patient's breast, and collect one or a plurality of tissue samples from within the patient's breast, all with just using a single hand. Such tissue samples may be deposited in tissue sample holder (150), and later retrieved from tissue sample holder (150) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein. Alternatively, an operator may grasp biopsy device (10) with more than one hand and/or with any desired assistance. In still other examples, biopsy device (10) can be configured to be secured to a table or other fixture without handheld operation.

In some settings, whether biopsy device (10) is handheld or mounted to a fixture, the operator may capture a plurality of tissue samples with just a single insertion of needle (110) into the patient's breast. Such tissue samples may be deposited in tissue sample holder (150), and later retrieved from tissue sample holder (150) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

Figure 2:
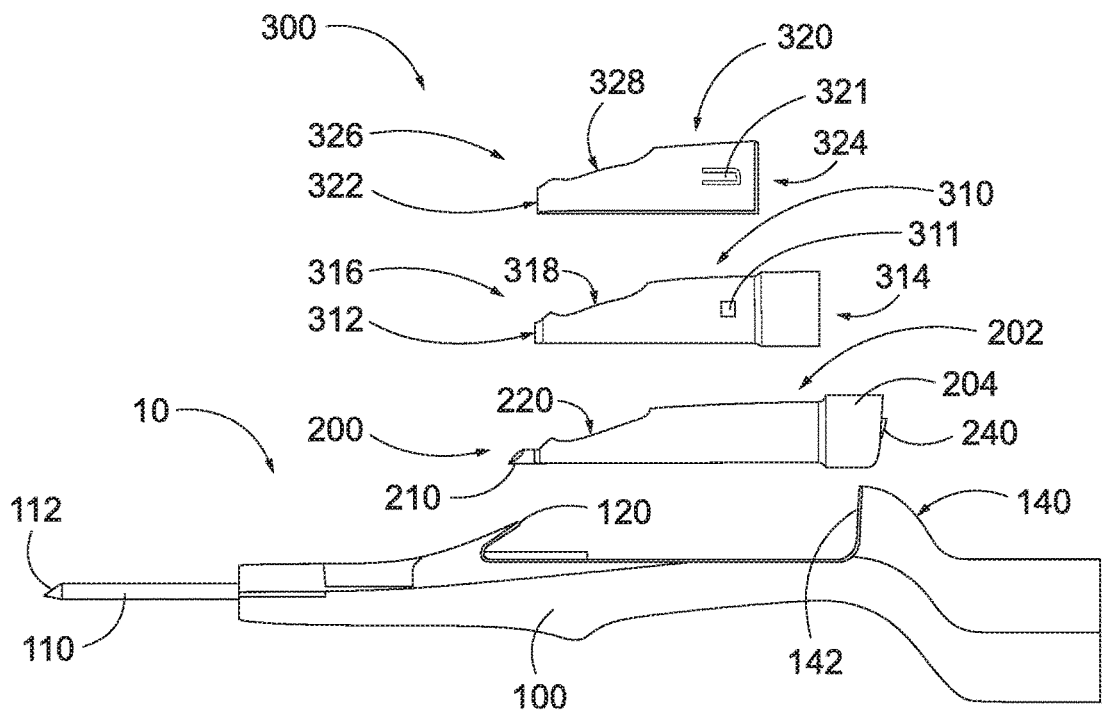
FIG. 2 depicts a partially exploded side elevation view of the biopsy device of FIG. 1, with the removable cover assembly separated into inner and outer retainers and decoupled from a holster.

As seen in FIG. 2, holster (200) of the present example includes an outer housing (202) that is configured to at least partially encompass the internal components of holster (200). Although not shown, it should be understood that holster (200) of the present example includes one or more motors and/or other actuators that are configured to drive various components of probe. To communicate power or movement to probe (100), holster (200) can include one or more gears. For instance, in some examples, one or more gears at least partially extend through an opening in outer housing (202). The opening in outer housing (202) can be configured to align with a corresponding opening associated with probe (100) to thereby permit the one or more gears of holster (200) to mesh with one or more corresponding gears of probe (100).

Although not shown, it should be understood that holster (200) may also include various cables that are configured to couple holster (200) to a control module or another control feature. Suitable cables may include electrical cables, rotary drive cables, pneumatic cables, or some combination thereof. Accordingly, it should be understood that in some examples, internal components within holster (200) may be powered by electrical power (electrical cables), rotary power (rotary drive cable), and/or pneumatic power (pneumatic cables). Alternatively, in some examples the cables are omitted entirely and holster (200) can be battery powered with motors and vacuum pumps being entirely contained within holster (200).

As described above with respect to holster (200), probe (100) is selectively couplable to holster (200) so that holster (200) may provide power or otherwise actuate probe (100). As can be best seen in FIG. 2, holster (200) includes a locating feature (210) at the distal end of holster (200). Holster (200) further includes a retention feature (240) at the proximal end of holster (200). Locating feature (210) is sized and configured to securely fit holster (200) into a corresponding receiving feature (120) of probe (100) when holster (200) is attached to an outer housing of probe (100). Retention feature (240) is sized and configured to securely attach holster (200) onto probe (100) by latching against a catch (142) of probe (100). Catch (142) includes a bore, aperture, or opening near a proximal end of probe (100) configured to receive retention feature (240). Latch (140) of probe (100) is positioned proximally to catch (142) and is in mechanical communication with catch (142) to thereby be operable to disengage catch (142) from retention feature (240) of holster (200). Upon actuating latch (140) and disengaging catch (142) from retention feature (240), holster (200) becomes decoupled from probe (100). Of course, a variety of other types of structures, components, features, etc. (e.g., bayonet mounts, clamps, clips, snap fittings, etc.) may be used to provide removable coupling of probe (100) and holster (200). While only a few exemplary attachment configurations have been described for holster (200), other various configurations may be provided as will be apparent to those of ordinary skill in the art in view of the teachings herein. Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Probe (100) of the present example further includes a needle (110) extending distally from probe (100) that is inserted into a patient's tissue to obtain tissue samples. These tissue samples are deposited in a tissue sample holder (150) at the proximal end of probe (100). In some examples, a vacuum control module (not shown) is coupled with probe (100) via a valve assembly (not shown) and tubes (not shown), which is operable to selectively provide vacuum, saline, atmospheric air, and venting to probe (100). By way of example only, the internal components of the valve assembly may be configured and arranged as described in U.S. Pat. Pub. No. 2013/0218047, entitled "Biopsy Device Valve Assembly," published Aug. 22, 2013, the disclosure of which is incorporated by reference herein.

Needle (110) of the present example comprises a cannula (113) having a piercing tip (112), and a lateral aperture (114) located proximal to tip (112). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. By way of example only, tip (112) may be configured in accordance with any of the teachings in U.S. Pat. No. 8,801,742, entitled "Needle Assembly and Blade Assembly for Biopsy Device," filed Jun. 1, 2011, the disclosure of which is incorporated by reference herein. As another merely illustrative example, tip (112) may be configured in accordance with at least some of the teachings in U.S. Pat. No. 9,486,186, entitled "Biopsy Device with Slide-In Probe," issued Nov. 8, 2016, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (not shown) having a sharp distal edge (not shown) is located within needle (110). Cutter is operable to rotate and translate relative to needle (110) and past lateral aperture (114) to sever a tissue sample from tissue protruding through lateral aperture (114). For instance, cutter may be moved from an extended position to a retracted position, thereby "opening" lateral aperture (114) to allow tissue to protrude therethrough; then from the retracted position back to the extended position to sever the protruding tissue.

In some examples, it may be desirable to rotate needle (110) to orient lateral aperture (114) at a plurality of desired angular positions about the longitudinal axis of needle (110). In the present example, needle (110) can be rotated by a motor disposed in probe (100) or holster (200). In other examples, needle (110) is manually rotatable by a thumbwheel on probe (100) or needle hub directly overmolded onto needle (110). Regardless, it should also be understood that, as with other components described herein, needle (110) may be varied, modified, substituted, or supplemented in a variety of ways; and that needle (110) may have a variety of alternative features, components, configurations, and functionalities. For instance, needle (110) may be constructed and operable in accordance with at least some of the teachings of U.S. Pat. No. 9,345,457, issued May 24, 2016, the disclosure of which is incorporated by reference herein; and/or in accordance with the teachings of any other reference cited herein.

Tissue sample holder (150) is selectively coupleable to the proximal end of probe (100). In some examples, tissue sample holder (150) may be configured to operate in two discrete sample collection modes—a bulk tissue collection mode and an individual tissue collection mode. By way of example only, tissue sample holder (150) may be constructed and operable in accordance with at least some of the teachings of U.S. application Ser. No. 15/829,499, entitled "Multi-Chamber Tissue Sample Cup for Biopsy Device," filed on Dec. 1, 2017, the disclosure of which is incorporated by reference herein. By way of further example, tissue sample holder (150) may be constructed and operable in accordance with at least some of the teachings of any of the other references cited herein; and/or in any other suitable fashion.

The distal portion of probe (100) further includes a tissue sample window (139) disposed proximally of the distal end of probe (100). In some examples, tissue sample window (139) exposes a gate assembly (not shown), such that the gate assembly is visible to an operator though probe (100). The gate assembly is generally configured to selectively arrest movement of the severed tissue sample within the fluid conduit between the cutter and the tissue sample holder (150). The gate assembly is enables the operator to temporarily cease progression of tissue samples for visual inspection though a sample window (139) of probe (100). At least a portion of the gate assembly is coupled to cutter to communicate rotational and translational motion of gate assembly to cutter. Thus, it should be understood that rotation and translation of cutter drive member (not shown) results in corresponding rotation and translation of cutter via the coupling between at least a portion of the gate portion and at least a portion of the gate assembly. In some examples, the gate assembly may be constructed in accordance with the teachings of U.S. application Ser. No. 15/829,483, entitled "Apparatus to Allow Biopsy Sample Visualization During Tissue Removal," filed on Dec. 1, 2017, the disclosure of which is incorporated by reference herein. Alternatively, probe (100) may simply lack a gate assembly, such that severed tissue samples are permitted to travel freely to tissue sample holder (150).

II. Exemplary Sterile Cover Assembly

As described above, holster (200) of the present example is configured as a reusable portion, while probe (100) is configured as a disposable portion. In some contexts, it may be desirable to maintain sterility of reusable components during a biopsy procedure. Accordingly, in some instances it may be desirable to use holster (200) in connection with certain shielding features to maintain the sterility of holster (200), while also maintaining functionality of holster (200). Although some suitable features for maintaining the sterility of holster (200) are described below, it should be understood that other alternative configurations may be used in connection with biopsy device (10) without departing from the teachings herein.

FIG. 1 shows an exemplary removable cover assembly (300) of the present example removably coupled to holster (200) to provide sterility protection of the various components of holster (200) and outer housing (202) of holster (200). In the present configuration, holster (200) is a reusable component, while removable cover assembly (300) is disposable. It should be understood that the use of the term "cover" herein should not be read as only requiring removable cover assembly (300) to be placed on top of outer housing (202) of holster (200). For instance, as will be discussed in greater detail below, in the present example removable cover assembly (300) includes a set of sleeves (310, 320, 330) that engage holster (200) to secure removable cover assembly (300) to biopsy device (10). Removable cover assembly (300) is sized and shaped to encase outer housing (202) of holster (200) and the various components of holster (200). Removable cover assembly (300) comprises an inner retainer (310) and an outer retainer (320). In its assembled configuration, inner retainer (310) is operable to contain holster (200) and outer retainer (320) is configured to encase or enclose at least a portion of inner retainer (310) while inner retainer (310) encases or enclose at least a portion of holster (200). In some versions, as will be discussed in further detail below, removable cover assembly (300) may further include a flexible sterile cover (330) configured to encase or enclose at least a portion of inner retainer (310) and at least a portion of holster (200) prior to their insertion within outer retainer (320).

As best seen in FIG. 2, inner retainer (310) includes a proximal inner retainer opening (314), a distal inner retainer opening (316), and a top inner retainer opening (318). Inner retainer (310) further includes an inner retainer channel (312) contained within the outer housing of inner retainer (310) and positioned between inner retainer openings (314, 316). Inner retainer (310) is sized and shaped to slidably receive holster (200) within inner retainer channel (312) through proximal inner retainer opening (314). Inner retainer (310) has a longitudinal length less than a longitudinal length of holster (200) such that a proximal end (204) of holster (200) extends proximally from proximal inner retainer opening (314).

Similar to inner retainer (310), outer retainer (320) includes a proximal outer retainer opening (324), a distal outer retainer opening (326), and a top outer retainer opening (328). Outer retainer (320) further includes an outer retainer channel (322) contained within the outer housing of outer retainer (320) and positioned between outer retainer openings (324, 326). Outer retainer (320) is sized and shaped to slidably receive inner retainer (310) within outer retainer channel (322) through proximal outer retainer opening (324). Outer retainer (320) has a longitudinal length less than the longitudinal length of inner retainer (310) such that a proximal end of inner retainer (310) extends proximally from proximal outer retainer opening (324). It should be understood that the longitudinal lengths of sleeves (310, 320) in relation to holster (200) may vary from those depicted as other suitable lengths for will be apparent to those of ordinary skill in the art.

Figure 3:
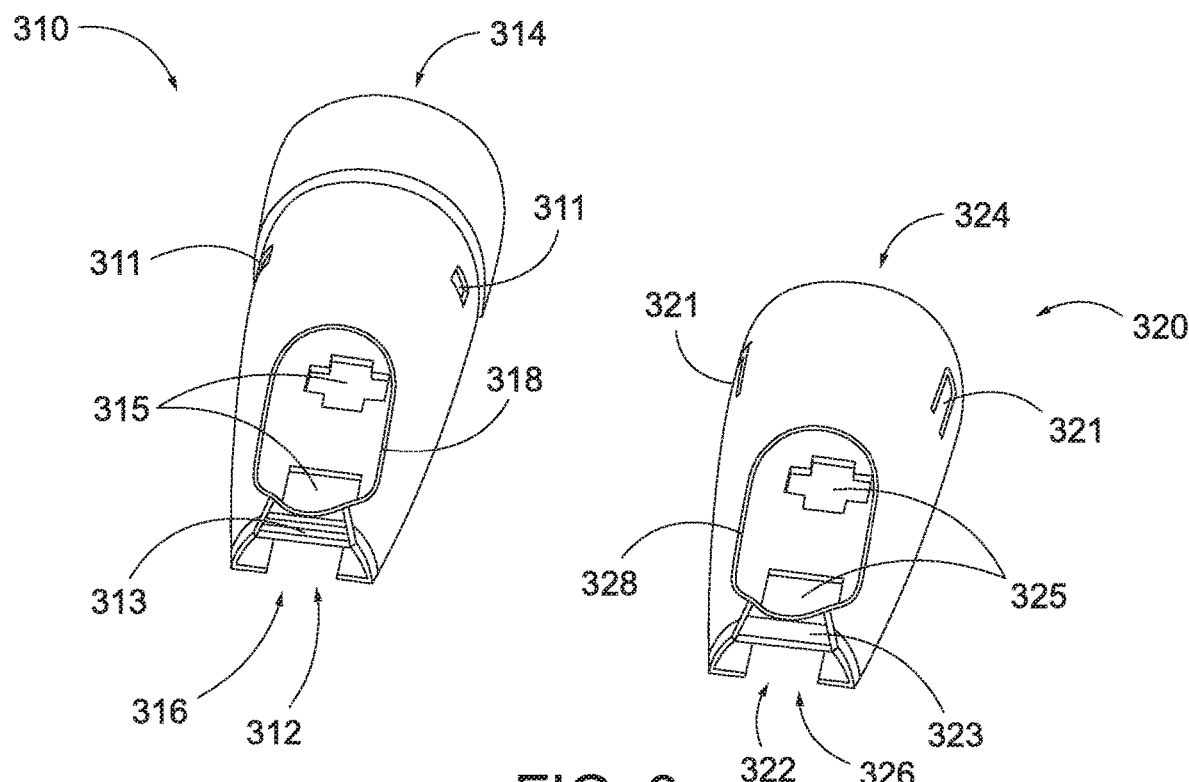
FIG. 3 depicts a perspective view of the inner and outer retainers of the removable cover assembly of FIG. 1, in a decoupled state.

In some variations of holster (200), outer housing (202) may include a series of buttons (not shown) or other operating control features on an operating panel (220) that allow an operator to actuate biopsy device (10) during a procedure. In this instance, it may be beneficial for the operator to maintain continued access to operating panel (220) while holster (200) is contained within removable cover assembly (300). In the present example, as seen in FIG. 3, top inner retainer opening (318) is positioned along the outer housing of inner retainer (310) and proximal to distal inner retainer opening (316). Top inner retainer opening (318) is sized and shaped to correspond with the size and shape of operating panel (220) to thereby provide continued access to operating panel (220) despite the positioning of holster (200) within inner retainer (310). Similarly, top outer retainer opening (328) is positioned along the outer housing of outer retainer (320) and proximal to distal outer retainer opening (326). Top outer retainer opening (328) is sized and shaped to correspond with the size and shape of top inner retainer opening (318) and operating panel (220) to provide continued access of operating panel (220) despite the positioning of holster (200) within sleeves (310, 320).

Operating panel (220) can include numerous operator interface features. For instance, in some examples operating panel (220) includes three outwardly protruding buttons. In such examples, each button can be assigned to activate a discrete operational feature. By way of example only, in some examples one button triggers opening and closing of lateral aperture (114), another button activates vacuum to pull fluid from needle (110), and another button can activate transport of a tissue sample through needle (110). Although certain discrete functions are described herein in relation to the buttons, it should be understood that in other examples numerous alternative functions may be controlled with buttons. In addition, in some examples buttons may be programable such that an operator may assign a function to each button from a plurality of different functions. In still other examples, the buttons may be eliminated entirely and replaced with one or more alternative control features such as a touchpad, a sensor, and/or etc.

Figure 4:
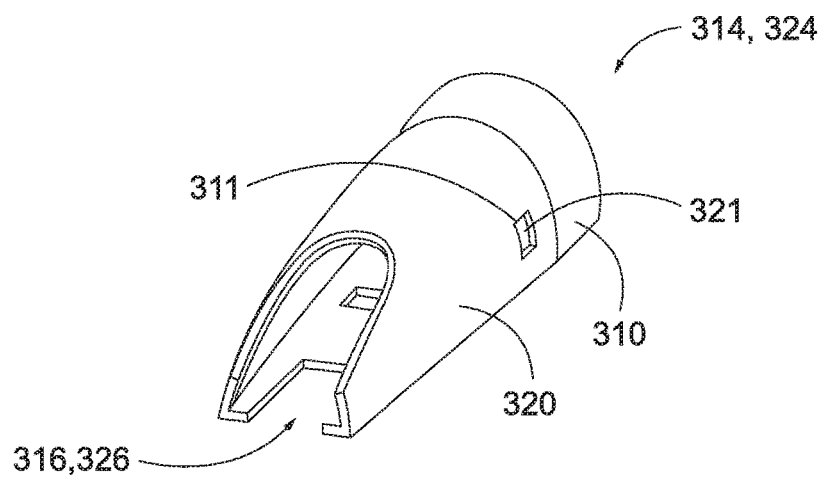
FIG. 4 depicts a perspective view of an exemplary alternative inner and outer retainers of the removable cover assembly of FIG. 1, in a coupled state.

As discussed above, holster (200) may further include one more or gears (not shown) or other interface features that provide for the mechanical communication between probe (100) and holster (200) when coupled together. In this instance, it may be beneficial for the one or more gears of holster (200) to maintain continued communication with probe (100) while holster (200) is contained within removable cover assembly (300). In the present example, as seen in FIGS. 3-4, sleeves (310, 320) include bottom sleeve openings (315, 325) along a bottom surface of sleeves (310, 320) opposite of top sleeve openings (318, 328). In particular, bottom sleeve openings (315) of inner retainer (310) are positioned along the outer housing of inner retainer (310) and proximal to distal inner retainer opening (316). Bottom inner retainer openings (318) are sized and shaped to correspond with the size and shape of the one or more gears (not shown) of holster (200) to provide the one or more gears continued access to probe (100) despite the positioning of holster (200) within inner retainer (310). Similarly, bottom outer retainer openings (325) are positioned along the outer housing of outer retainer (320) and proximal to distal outer retainer opening (326). Bottom outer retainer openings (325) are sized and shaped to correspond with the size and shape of bottom inner retainer openings (315) and the one or more gears of holster (200) to provide them continued access to probe (100) despite the positioning of holster (200) within sleeves (310, 320).

As previously discussed, holster (200) is configured to couple to probe (100) through the engagement of locating feature (210) of holster (200) with receiving feature (120) of probe (100) and retention feature (240) of holster (200) with catch (142) of probe (100). To accommodate the continued ability for holster (200) to removably attach to probe (100), despite being positioned within removable cover assembly (300), sleeves (310, 320) include sleeve openings (314, 316, 324, 326) on both distal and proximal ends, respectively, as seen in FIG. 4. In particular, sleeves (310, 320) include distal sleeve openings (316, 326) which are sized and shaped to receive the distal end of holster (200) when holster (200) is slidably received within removable cover assembly (300). In this instance, locating feature (210) may extend through distal sleeve openings (316, 326) and beyond sleeves (310, 320) to thereby allow locating feature (210) to engage receiving feature (120) despite holster (200) being protectively contained within sleeves (310, 320).

Furthermore, sleeves (310, 320) include proximal sleeve openings (314, 324) which are sized and shaped to allow the distal end of holster (200) to extend beyond sleeves (310, 320) when holster (200) is slidably received within removable cover assembly (300). In this instance, retention feature (240) is positioned proximally from proximal sleeve openings (314, 324) and outside of sleeves (310, 320) to thereby allow retention feature (240) to engage catch (142) despite holster (200) being protectively contained within sleeves (310, 320). Alternatively, sleeves (310, 320) may include sleeve locating features (313, 323) at distal sleeve openings (316, 322), respectively as seen in FIG. 3. Sleeve locating features (313, 323) are sized, shaped and configured to engage receiving feature (120) in place of locating feature (210) of holster (200). In this instance, holster (200) and removable cover assembly (300) still becomes securely coupled to probe (100) despite holster (200) being protectively contained within sleeves (310, 320).

As further seen in FIGS. 2-4, inner retainer (310) further includes a recess (311) positioned along the outer housing of inner retainer (310). Outer retainer (320) includes a tab (321) protruding inwardly away from the outer housing of outer retainer (320) and into outer retainer channel (322). Tab (321) may be positioned along outer retainer (320) to correspond with the position of recess (311) on the outer housing of inner retainer (310). Tab (321) is configured to releasably engage recess (311) to thereby removably attach outer retainer (320) to inner retainer (310) when inner retainer (310) is slidably inserted within outer retainer (320). Once engaged with each other, recess (311) is configured to releasably hold tab (321) until the operator exerts a predetermined releasing force on outer retainer (320) in the distal direction, or alternatively on inner retainer (310) in the proximal direction. Exerting the predetermined releasing force on either sleeve (310, 320) causes tab (321) to press against the perimeter walls of recess (311) until the protrusion of tab (321) is forced laterally outward from recess (311) thereby releasing outer retainer (320) from the secured engagement with inner retainer (310). At this point, inner retainer (310) may be slidably removed from outer retainer (320).

In the present example, recess (311) and tab (321) are positioned near the proximal end of sleeves (310, 320), respectively. It will be apparent to those of ordinary skill in the art that recess (311) and tab (321) may be positioned along the outer housing of sleeves (310, 320) at various other suitable positions. Alternatively, it should be understood that additional recesses (311) and tabs (321) may be included on sleeves (310, 320) than those shown. Furthermore, as seen in FIG. 4, recess (311) may be included on outer retainer (320) and tab (321) may be included on inner retainer (311). Although not shown, it should further be understood that recess (311) and tab (321) may be in the form of other various fastener configurations or operabilities that provide for the releasable attachment of inner retainer (310) to outer retainer (320) as will be apparent to those of ordinary skill in the art in view of the teachings herein.

Figure 5:
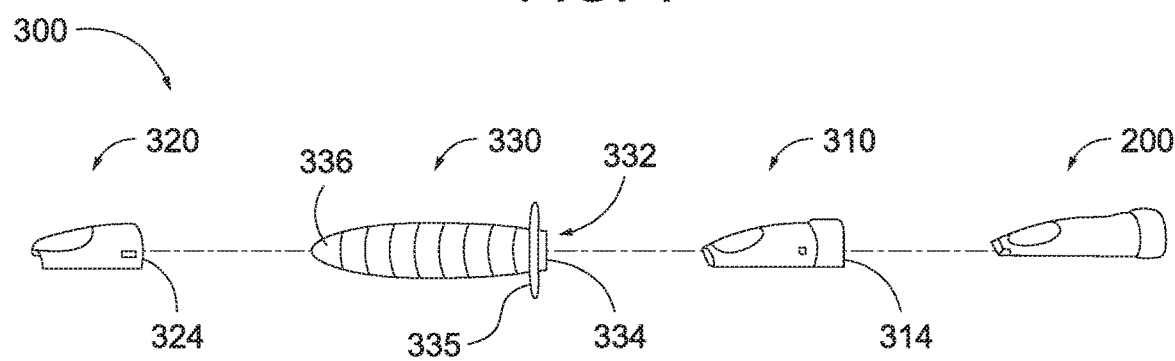
FIG. 5 depicts an exploded view of the sterile sleeve assembly of FIG. 1, with the removable cover assembly including an exemplary flexible sterile cover, with the removable cover assembly decoupled from the holster.

FIG. 5 shows an exploded view of removable cover assembly (300) and holster (200). As previously discussed, holster (200) is slidably received within inner retainer (310) through proximal inner retainer opening (314); which in turn is slidably received within outer retainer (320) through proximal outer retainer opening (324). In the present example, however, inner retainer (310) is slidably received within flexible sterile cover (330), rather than directly into outer retainer (320). Flexible sterile cover (330) is sized and shaped to slidably receive and encase inner retainer (310) and holster (200) without requiring an adhesion process. Once inner retainer (310) and holster (200) are fully encased within flexible sterile cover (330), flexible sterile cover (330) may be slidably received within outer retainer (320). It should be understood that removable cover assembly (300) is further configured to be preassembled such that outer retainer (320), flexible sterile cover (330) and inner retainer (310) are respectively attached to each other prior to holster (200) being inserted into removable cover assembly (300). Although the present example is shown as including flexible sterile cover (330), it should be understood that in some examples flexible sterile cover (330) is omitted and only inner retainer (310) and outer retainer (320) are used with holster (200).

As will be described in greater detail below, flexible sterile cover (330) generally defines a negligible thickness such that flexible sterile cover (330) does not inhibit coupling between probe (100) and holster (200). The term "negligible" used herein is used to refer to minimal interference between probe (100) and holster (200) such that probe (100) and holster (200) can still couple to each other through the thickness of outer sleeve (330). It should be understood that a negligible thickness may vary depending on a variety of factors such as the space between probe (100) and holster (200) or the types of couplings used. For instance, in some examples flexible sterile cover (330) defines a thickness of about 0.048 mm. In other examples, flexible sterile cover defines a thickness of 0.072 mm. Still in other examples, flexible sterile cover (330) defines a thickness of 0.08 mm. In yet other examples, flexible sterile cover (330) defines a relatively thick material having a thickness of approximately 0.25 mm. In yet other examples, flexible sterile cover (330) defines a thickness of 3 mm or less. Regardless of the particular thickness of flexible sterile cover (330), it should be understood that flexible sterile cover (330) also comprises a material exhibiting elastomeric properties that permit flexible sterile cover (330) to bend, stretch, and contour around various geometric features of holster (200). Accordingly, in circumstances where flexible sterile cover (330) is stretched, it should be understood that the thickness of flexible sterile cover (330) can correspondingly decrease in response to such stretching.

Flexible sterile cover (330) comprises a flexible sleeve channel (332), a proximal flexible sleeve opening (334), and a distal flexible sleeve end (336). Flexible sleeve channel (332) is contained within the outer layer of flexible sterile cover (330) and is defined between proximal flexible sleeve opening (334) and distal flexible sleeve end (336). Proximal flexible sleeve opening (334) is sized and shaped to slidably receive holster (200) contained within inner retainer (310). Distal flexible sleeve end (336) is sized and shaped to contain inner retainer (310) while not interfering with the ability of inner retainer (310) from being slidbaly received within outer retainer (320).

Although not shown, it should be understood that in some instances proximal flexible sleeve opening (334) can be equipped with a sleeve ring (335). A suitable sleeve ring (335) can be configured to promote manipulation of proximal flexible sleeve opening (334) while still permitting access to flexible sleeve channel (322). One such suitable sleeve ring (335) can be a flange extending outwardly relative to flexible sleeve opening (334). Such a flange can provide a gripping surface around the perimeter of flexible sleeve opening (334) to permit an operator to manipulate flexible sterile cover (330). In another suitable sleeve ring (335), such a sleeve ring can include an attachment ring and a manipulation grip. In such a sleeve ring, the attachment ring can secure to the perimeter of flexible sleeve opening (334). Additionally, the manipulation grip can extend from at least a portion of the attachment ring to promote manipulation of flexible sterile cover (330) via the attachment ring. Of course, other suitable configurations for sleeve ring (335) can be used as will be apparent to those of ordinary skill in the art in view of the teachings herein.

Flexible sterile cover (330) may be formed of a material of latex, silicone, polyurethane, polyisoprene, nitrile, natural rubber or other various suitable materials that provide for a thin, flexible, durable, and sterile barrier between the sleeve's outer surface and inner surface. Flexible sterile cover (330) includes a thin thickness to an extent where the presence of flexible sterile cover (330) around inner retainer (310) and holster (200) is minimal and/or negligible. Thus, it should be understood that flexible sterile cover (330) is generally configured to surround locating feature (210) and retention feature (240) of holster (200) without substantially interfering with the coupling between holster (200) and probe (100). Incorporating removable cover assembly (300) onto holster (200) eliminates the need for adding a sterile barrier onto biopsy device (10) through an adhesion process, which can substantially reduce costs.

Figure 6:
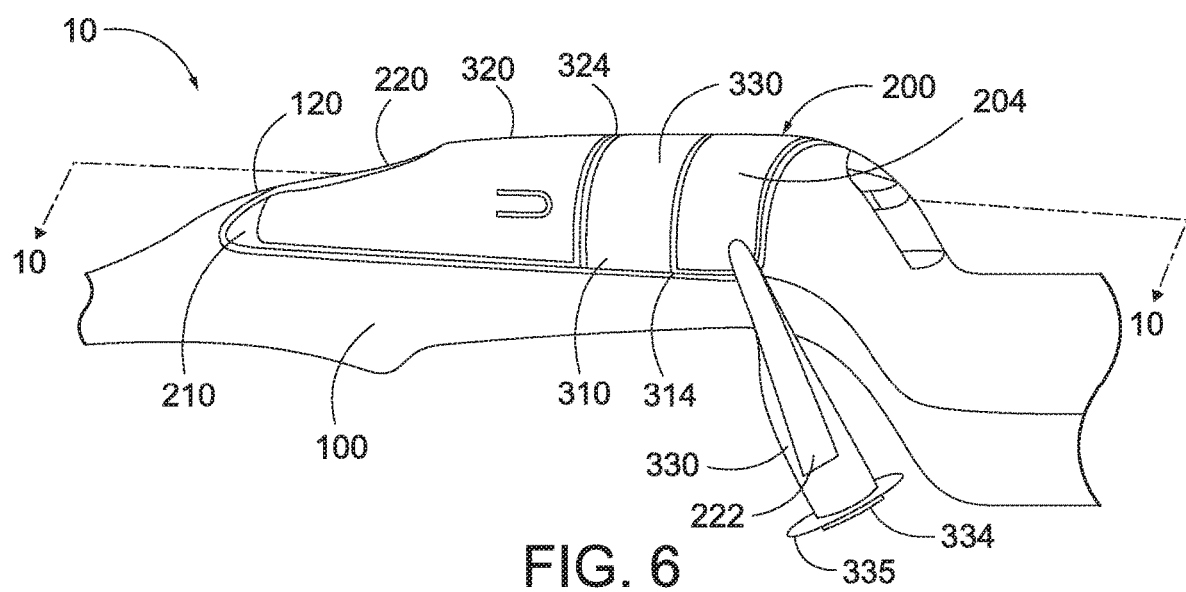
FIG. 6 depicts a perspective view of the biopsy device of FIG. 1 coupled to the removable cover assembly and contained within the flexible sterile cover.

As best seen in FIG. 6 flexible sterile cover (330) has a longitudinal length greater than the longitudinal lengths of inner retainer (310) and holster (200) such that the proximal end (204) of holster (200) is contained within proximal flexible sleeve opening (334) despite proximal end (204) extending beyond proximal sleeve openings (314, 324). In the present example, proximal flexible sleeve opening (334) extends beyond proximal end (204) to further encase a series of holster cables (222) to thereby allow the operator to maintain sterility of both holster (200) and holster cables (222). This may be beneficial as holster cables (222) are as likely to be exposed to non-sterile substances during a biopsy procedure as holster (200). In some examples, the length of flexible sterile cover (330) can be approximately two times the length of biopsy device (10). In other examples, the length of flexible sterile cover (330) can be approximately three feet. In such examples, a length of three feet provides approximately two and a half feet of coverage of holster cables (222). In either example, it is generally desirable to have a sufficient length such that the coverage of flexible sterile cover (330) over holster cables (222) covers approximately the entire patient window. In other words, the length of flexible sterile cover (330) is generally of sufficient length to avoid direct contact between holster cables (222) and the patient as well as other procedure room equipment associated with the patient (e.g., the patient table). Of course, other suitable lengths for flexible sterile cover (330) will be apparent to those of ordinary skill in the art in view of the teachings herein.

By encompassing holster (200), flexible sterile cover (330) becomes positioned between the engagement mechanisms (120, 142) that allow holster (200) to couple with probe (100). In particular, flexible sterile cover (330) is positioned on a distal end between locating feature (210) of holster (200) and the corresponding receiving feature (120) of probe (100). Similarly, flexible sterile cover (330) is positioned on a proximal end between retention feature (240) of holster (200) and the corresponding catch (142) of probe (100).

Figure 7:
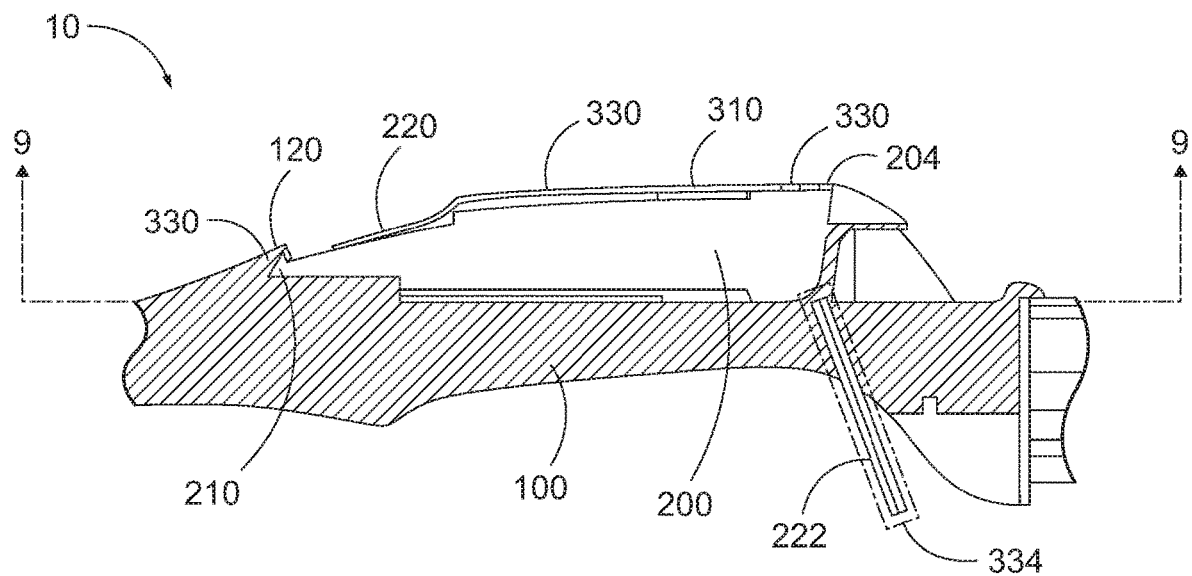
FIG. 7 depicts a side cross-sectional view of the biopsy device of FIG. 1, with the cross-section taken along line 7-7 of FIG. 1.
Figure 8:
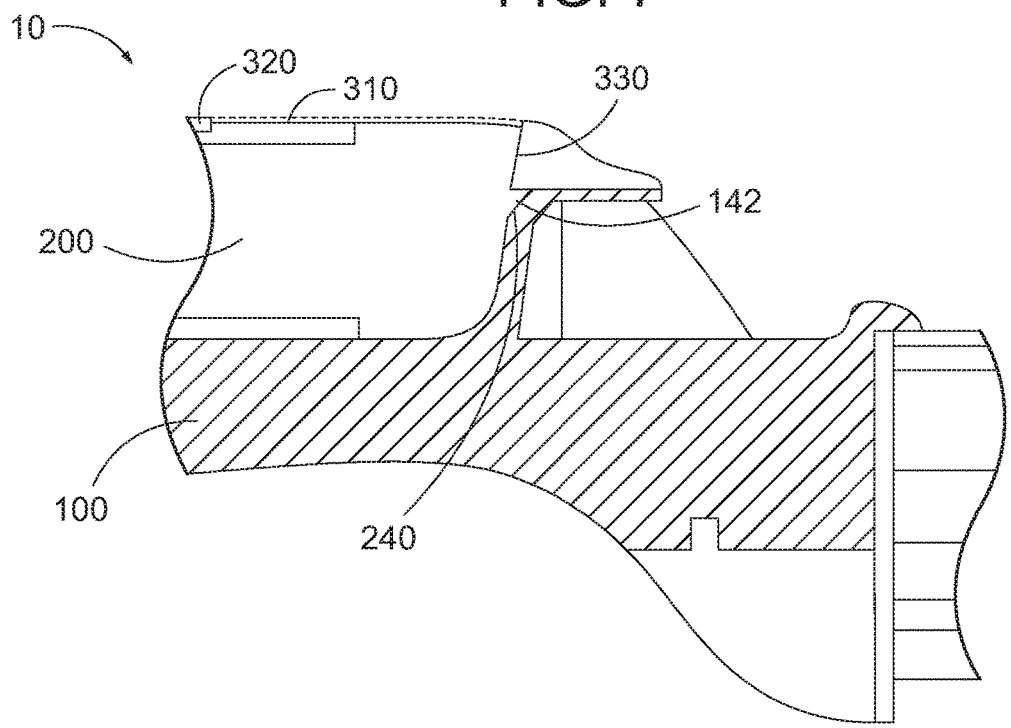
FIG. 8 depicts a side cross-sectional view of the holster latch coupled to the biopsy device of FIG. 1, with the flexible sterile cover positioned therebetween, with the cross-section taken along line 8-8 of FIG. 1.

However, as seen in FIG. 7, and as discussed above, flexible sterile cover (330) is formed of a thin, flexible material so as to not interfere with the corresponding engagement of holster (200) to probe (100). As such, flexible sterile cover (330) is configured to allow holster (200) to effectively couple with probe (100) despite being position therebetween. In particular, locating feature (210) maintains its ability to engage receiving feature (120) of probe (100) while flexible sterile cover (330) encases inner retainer (310) and locating feature (210) of holster (200). Similarly, as seen in FIG. 8, retention feature (240) maintains its ability to engage catch (142) of probe (100) while flexible sterile cover (330) encases inner retainer (310) and retention feature (240) of holster (200).

To further facilitate coupling, in the present example probe (100) and holster (200) form a gap between each other when coupled together at the bottom surface of holster (200). In the present example, this gap is approximately equivalent to the combined thickness of inner retainer (310), outer retainer (320), and flexible sterile cover (330). By way of example only, inner retainer (310) and outer retainer (320) can both have a thickness of approximately 1 mm. When combined with the thickness of flexible sterile cover (330), the total combined thickness can be as much as 2.28 mm or as little as 2.048 mm. Thus, in some examples the gap defined between probe (100) and holster (200) is at least 2.28 mm to accommodate the maximum combined thickness of inner retainer (310), outer retainer (320), and flexible sterile cover (330). In other examples, the gap defined between probe (100) and holster (200) is at least 2.048 mm to accommodate the minimum combined thickness of inner retainer (310), outer retainer (320), and flexible sterile cover (330). However, in some examples this gap can be increased even further than described above to provide an oversized clearance fit between probe (100) and holster (200). In examples with such an oversized clearance fit, the gap can be as much as 2.4 mm. Of course, since the gap defined by probe (100) and holster (200) is related to the thicknesses of sleeves (310, 320, 330), it should be understood that in examples where any one or more of these thicknesses are varied, the gap between probe (100) and holster (200) can be correspondingly varied to accommodate differently sized sleeves (310, 320, 330).

Figure 9:
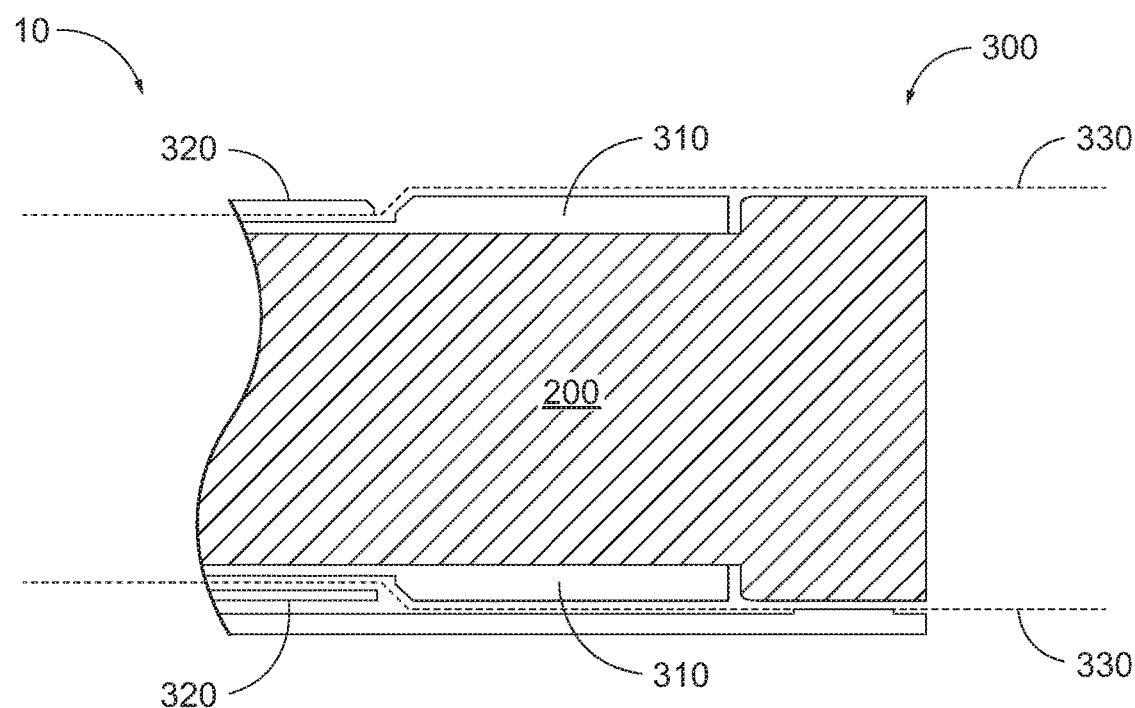
FIG. 9 depicts a bottom cross-sectional view of the biopsy device of FIG. 1, with the cross-section taken along line 9-9 of FIG. 7.
Figure 10:
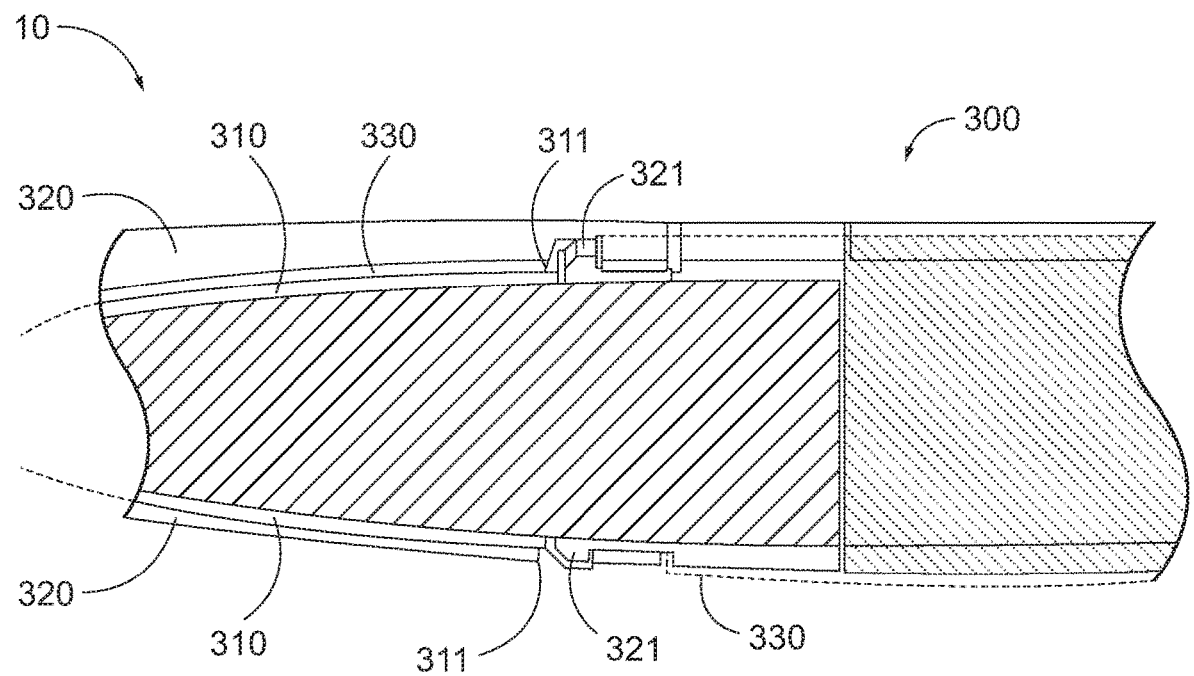
FIG. 10 depicts a perspective cross-sectional view of the outer retainer coupled to the inner retainer of the removable cover assembly of FIG. 1, with the flexible sterile cover positioned therebetween, with the cross-section taken along line 10-10 of FIG. 6.

FIG. 9 shows flexible sterile cover (330) positioned between outer retainer (320) and inner retainer (310). As seen, flexible sterile cover (330) is configured to allow inner retainer (310) to effectively slide within outer retainer channel (322) despite being positioned therebetween. As best seen in FIG. 10, tab (321) of outer retainer (320) maintains its ability to engage recess (311) of inner retainer (310) while flexible sterile cover (330) encases inner retainer (310) and recess (311).

Holster (200) of biopsy device (10) is configured to be a reusable portion while probe (100) is configured to be a disposable portion. Removable cover assembly (300) is thus configured to cover and protect holster (200) to maintain the sterility of holster (200) during a biopsy procedure. Removable cover assembly (300) includes multiple layers of shielding to maintain the sterility of holster (200), including outer retainer (320), flexible sterile cover (330) and inner retainer (310).

In an exemplary use, removable cover assembly (300) may be pre-assembled prior to a biopsy procedure. Pre-assembly may be completed by inserting inner retainer (310) into flexible sterile cover (330). Once inner retainer (310) is inserted therein, outer retainer (320) is inserted over the combination of flexible sterile cover (330) and inner retainer (310). Alternatively, the combination of flexible sterile cover (330) and inner retainer (310) is inserted into outer retainer (320). In either case, this causes tab (321) of outer retainer (320) to engage recess (311) of inner retainer (310) to thereby secure inner retainer (310) to outer retainer (320) with flexible sterile cover (330) disposed therebetween.

Once the components (310, 320, 330) of removable cover assembly (300) are assembled together, holster (200) may be slidably inserted into removable cover assembly (300) prior to attaching holster (200) to probe (100). Prior to insertion of holster (200), it should be understood that flexible sterile cover (330) may be at least partially rolled around a portion of the proximal end of inner retainer (310). This configuration may permit the interior of inner retainer (310) to be readily accessible for insertion of holster (200). Once holster (200) is inserted into inner retainer (310), the rolled portion of flexible sterile cover (330) may be unrolled around holster and/or cables (222) extending from holster (200).

The combination of removable cover assembly (300) and holster (200) is next coupled to probe (100). As described above, despite removable cover assembly (300) enclosing outer housing (202) of holster (200), removable cover assembly (300) is configured to allow locating feature (210) and retention feature (240) of holster (200) to effectively engage probe (100) through flexible sterile cover (330). In this instance, proximal sleeve openings (314, 324) and distal sleeve openings (316, 326) are configured to allow locating feature (210) and retention feature (240), respectively, to attach holster (200) to probe (100) with holster (200) fully encased within removable cover assembly (300).

Once holder (200) is coupled to probe (100), a biopsy procedure may be initiated. During such a biopsy procedure, it may be desirable to control various operational functions of biopsy device (10) via operating panel (220) of holster (200). As described above, removable cover assembly (300) is configured to maintain the functionality of operating panel (220) of holster (200) with holster (200) encased in removable cover assembly (300). Accordingly, in the present use top sleeve openings (318, 328) of removable cover assembly (300) provide accessibility to operating panel (220) with holster (200) received within removable cover assembly (300). Additionally, flexible sterile cover (330) is configured to surround locating feature (210), retention feature (240) and operating panel (220) of holster (200) without substantially interfering with their respective functionalities. Accordingly, removable cover assembly (300) allows holster (200) to maintain functionality while providing a shielding barrier over outer housing (202) and cables (222) to maintain the sterility of holster (200) throughout the biopsy procedure.

III. Exemplary Alternative Sleeve Ring

As described above, in some examples it may be desirable to secure a structure such as sleeve ring (335) to flexible sterile cover (330) to provide enhanced manipulation of flexible sterile cover (330). As described above, in some examples suitable sleeve rings may be configured as a simple flange. However, in some contexts additional features may be desirable. For instance, due to the flexible nature of flexible sterile cover (330), it may be desirable to equip suitable sleeve rings with fasteners, couplers, fittings, and/or etc. In addition, or in the alternative, in some contexts it may be desirable to control excess material of flexible sterile cover (330), particularly when flexible sterile cover (330) is not being completely utilized. Thus, in some examples it may be desirable to use a portion of a suitable sleeve ring to control excess material associated with flexible sterile cover (330).

Various examples of suitable sleeve rings similar to sleeve ring (335) are described below. Although certain specific examples are described below of various suitable manipulation, it should be understood that various alternative configurations may be used. In addition, to the extent that discrete features are described below in the context of specific embodiments, it should be understood that such features may be combined with other features in one or more alternative embodiments. Still other suitable sleeve rings will be apparent to those of ordinary skill in the art in view of the teachings herein.

Figure 12:
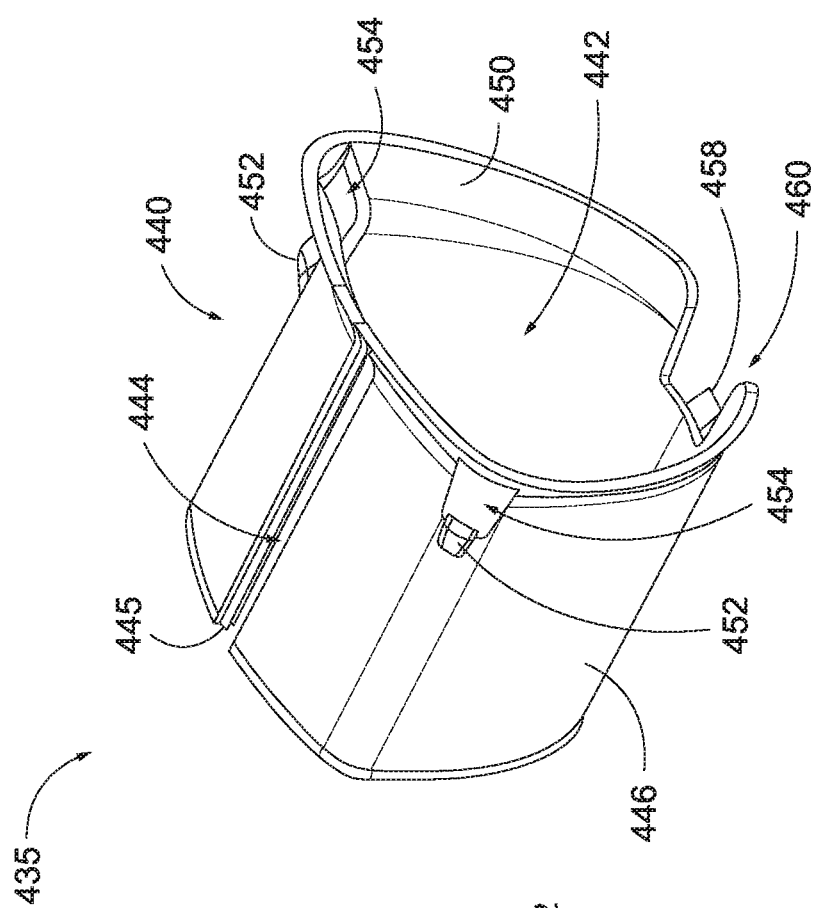
FIG. 12 depicts another perspective view of the sleeve ring of FIG. 11.
Figure 11:
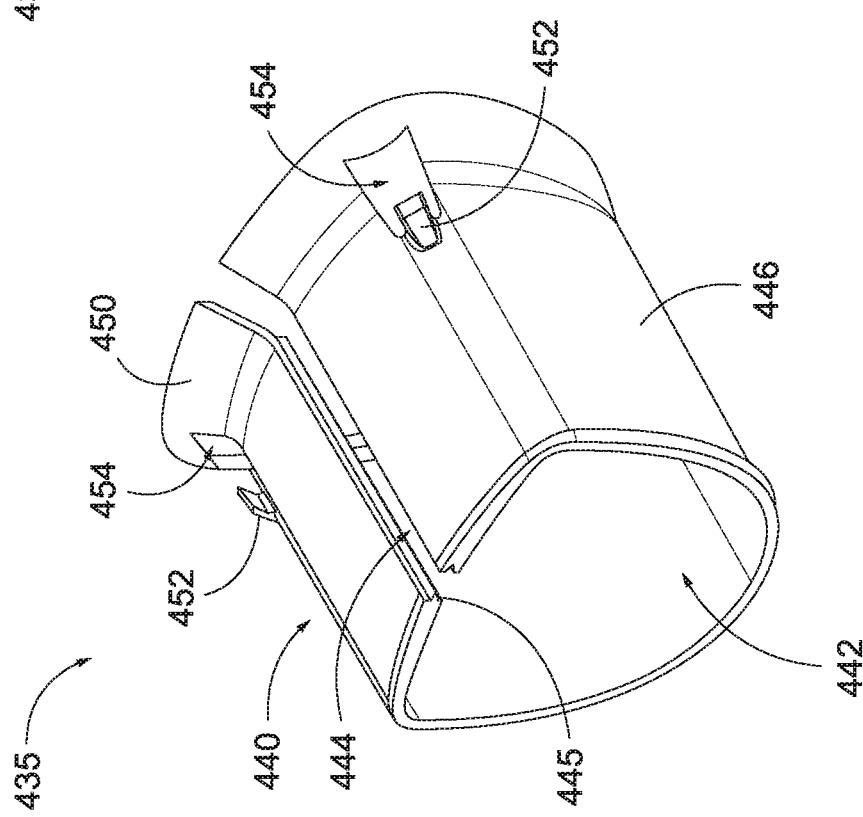
FIG. 11 depicts a perspective view of an exemplary alternative sleeve ring that can used with the flexible sterile cover of FIG. 5.

FIGS. 11 and 12 show an exemplary sleeve ring (435) or sleeve ring that may be readily used with flexible sterile cover (330) in lieu of sleeve ring (335) described above. Sleeve ring (435) is generally configured fasten to flexible sterile cover (330) to enhance the manipulation of flexible sterile cover (330). Sleeve ring (435) includes a body (440) that defines a sheath portion (446) and a horn portion (450). Body (440) is generally configured to receive inner retainer (310). In particular, body (440) is shown as defining a hollow interior (442) that forms a d-shape that generally corresponds to the shape of inner retainer (310). Although body (440) is shown and described herein as having a particular shape, it should be understood that in other examples, the shape of body (440) can be modified to any other suitable shape corresponding to the shape of inner retainer (310).

Body (440) defines a relief slot (444) extending longitudinally along the length of body (440). Body (440) is generally comprises of a thin relatively flexible material such as a plastic or polymer. Thus, body (440) has at least some flexibility. To further enhance this flexibility, relieve slot (444) is generally configured to permit a portion of body (440) to fold over onto itself to thereby reduce the size of body (440). As will be described in greater detail below, this configuration is generally desirable to promote attachment of flexible sterile cover (330) to sleeve ring (435).

Relief slot (444) includes an interlocking portion (445) defined by body (440) on either side of relief slot (444). As will be described in greater detail below, interlocking portion (445) is generally configured to provide some rigidity to body (440) when body (440) is compressed to close relieve slot (444). In the present example, interlocking portion (445) includes a tongue and groove configuration comprising a triangular tongue and corresponding triangular groove. In other examples, other suitable interlocking features can be used such as a square tongue and a square groove, a rounded tongue and a rounded groove, and/or etc.

Sheath portion (446) defines a substantial portion of the longitudinal length of body (440). Sheath portion (446) is generally configured to hold a portion of flexible sterile cover (330) in a compressed or folded configuration. As will be described in greater detail below, this feature may be desirable to manage excess portions of flexible sterile cover (330) when flexible sterile cover (330) is not in use. Sheath portion (446) can define a variety of suitable lengths. For instance, in some examples sheath portion (446) is approximately equivalent to ⅓ of the length of holster (200). In still other examples, sheath portion (446) is approximately equivalent to ¼ of the length of holster (200). Still other suitable lengths of sheath portion (446) will be apparent to those of ordinary skill in the art in view of the teachings herein.

Horn portion (450) extends proximally and outwardly relative to sheath portion (446). As can be seen, horn portion (450) provides a generally frustoconical shape. In other words, horn portion (450) is generally flared outwardly relative to sheath portion (446). This configuration provides an enlargement of hollow interior (442) of body (440) to thereby enhance access to hollow interior (442). As will be described in greater detail below, enhanced access may be desirable to aid in inserting components such as inner retainer (310) and/or holster (200) into sleeve ring (435) and into flexible sterile cover (330). Additionally, the flared nature of horn portion (450) provides enhanced gripping of sleeve ring (435) to thereby enhance manipulation of flexible sterile cover (330).

Sleeve ring (435) further includes a plurality of tabs (452, 458) extending proximally and outwardly from body (440) near the interface between sheath portion (446) and horn portion (450). Tabs (452, 458) are generally configured to grip at least a portion of flexible sterile cover (330) to provide releasable attachment between sleeve ring (435) and flexible sterile cover (330). As will be described in greater detail below, flexible sterile cover (330) generally extends distally from sleeve ring (435) when attached thereto. Thus, tabs (452, 458) extend in a proximal direction relative to body (440) while also extending outwardly. This configuration permits a portion of flexible sterile cover (330) to fold over and underneath tabs (452, 458) to releasably hold flexible sterile cover (330) in position.

In the present example, tabs (452, 458) include a pair of upper tabs (452) and a single lower tab (458). Lower tabs (452) are positioned at the upper inflexion points in the shape of body (440). Meanwhile lower tab (458) is positioned at the lower inflexion point in the shape of body (440). Although upper tabs (452) and lower tab (458) are described separately herein, it should be understood that upper tabs (452) and lower tab (458) are generally substantially similar to each other except as where otherwise noted herein.

Beneath each tab (452, 458), body (440) defines an opening (454, 460) associated with each tab (452, 458). Openings (454, 560) are generally configured to provide additional clearance that permits flexible sterile cover (330) to fully engage each tab (452, 458). For instance, in the absence of openings (454, 460), the curvature of horn portion (450) could potentially interfere with engagement between flexible sterile cover (330) and tabs (452, 458) by flexible sterile cover (330) riding up the curvature of horn portion (450).

Openings (454, 460) include a pair of upper openings (454) and a single lower opening (460). Upper openings (454) are associated with upper tabs (452). Meanwhile, lower opening (460) is associated with lower tab (458). Each upper opening (454) is enclosed on all four sides of the rectangular shape defined by each upper opening (454). This configuration is generally due to the curvature of horn portion (450) in the area associated with upper openings (454). In particular, since the curvature of horn portion (450) is relatively steep in the area associated with upper openings (454), it is desirable to entirely enclose upper openings (454). Meanwhile, the proximal face of lower opening (460) is open due to the relatively low slope of the curvature of horn portion (450) in the area associated with lower opening (460).

Figure 13:
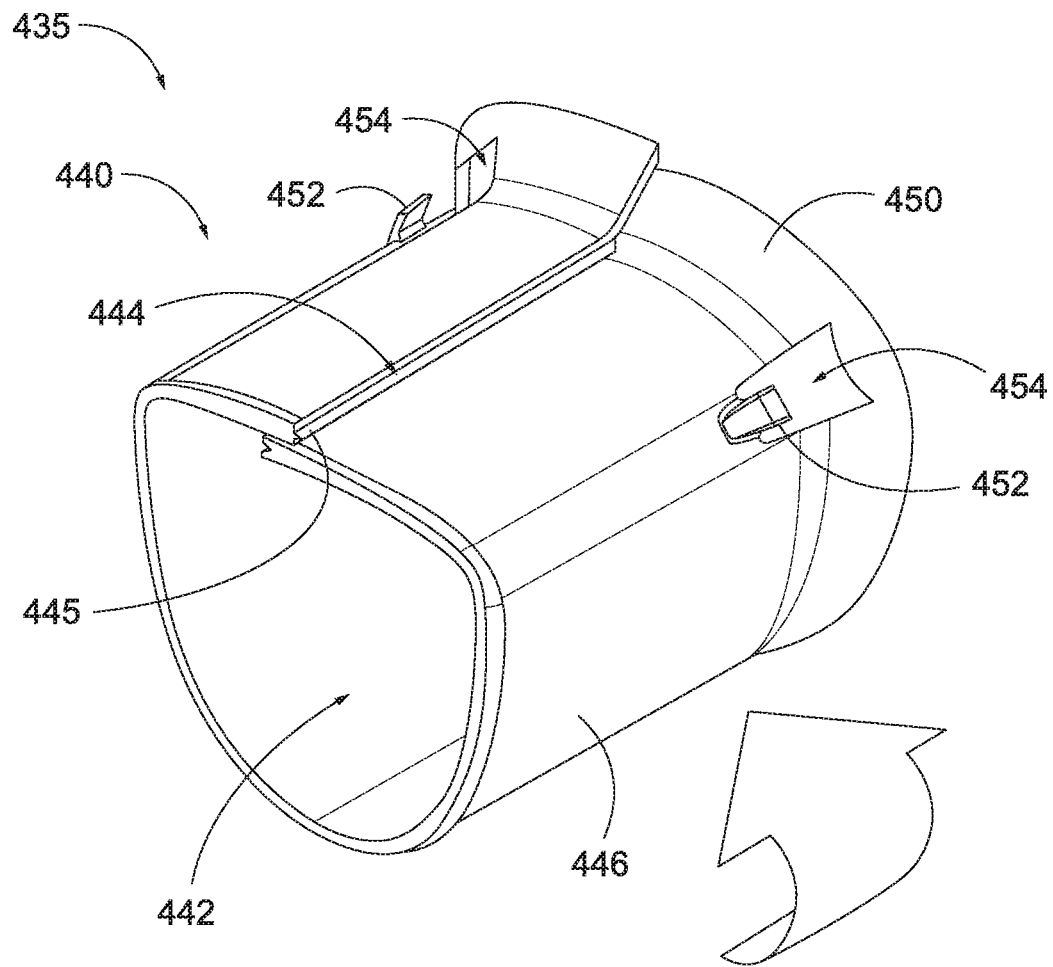
FIG. 13 depicts still another perspective view of the sleeve ring of FIG. 11, the sleeve ring in a flexed configuration.
Figure 14:
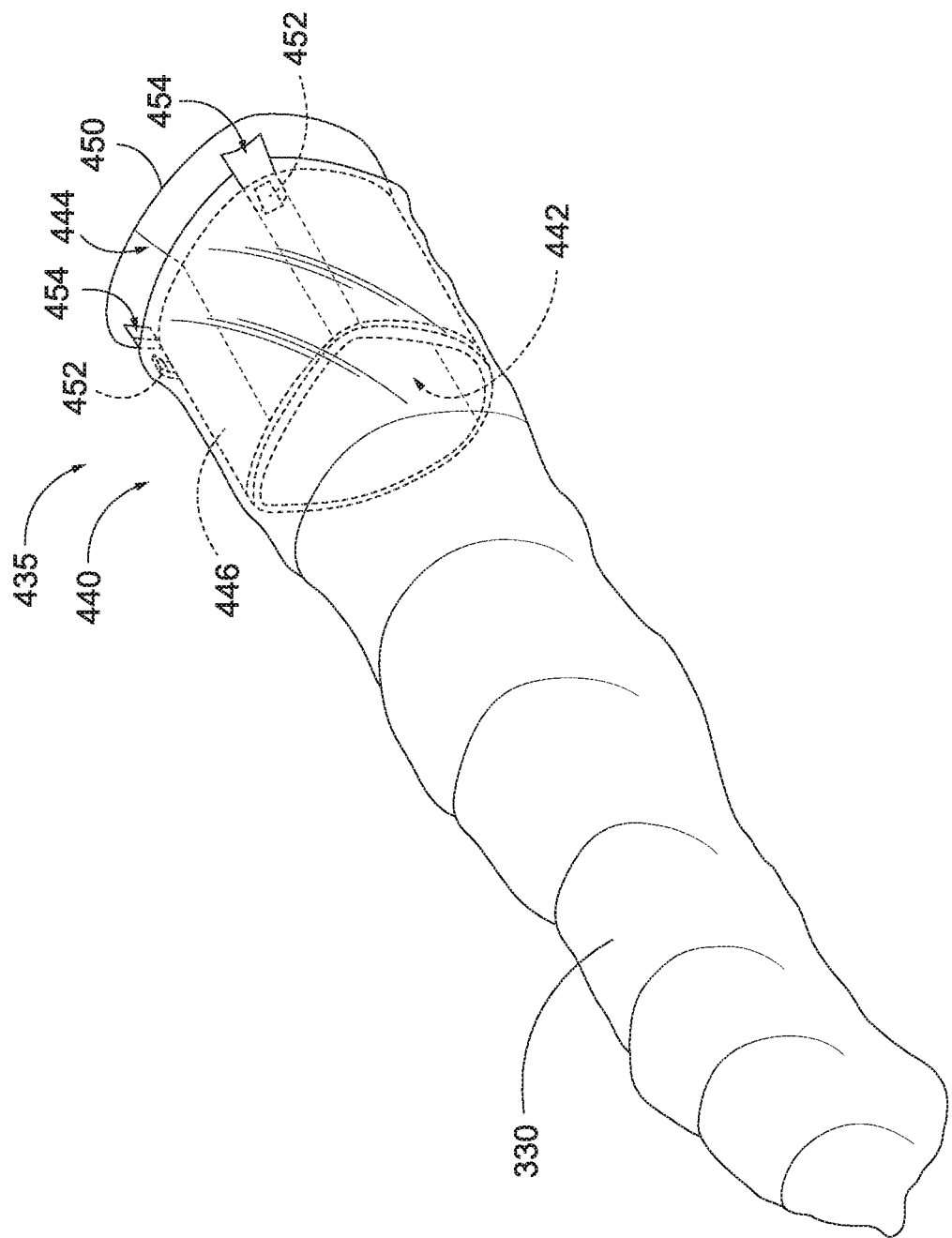
FIG. 14 depicts yet another perspective view of the sleeve ring of FIG. 11, with the flexible sterile cover secured thereto and in an extended configuration.
Figure 15:
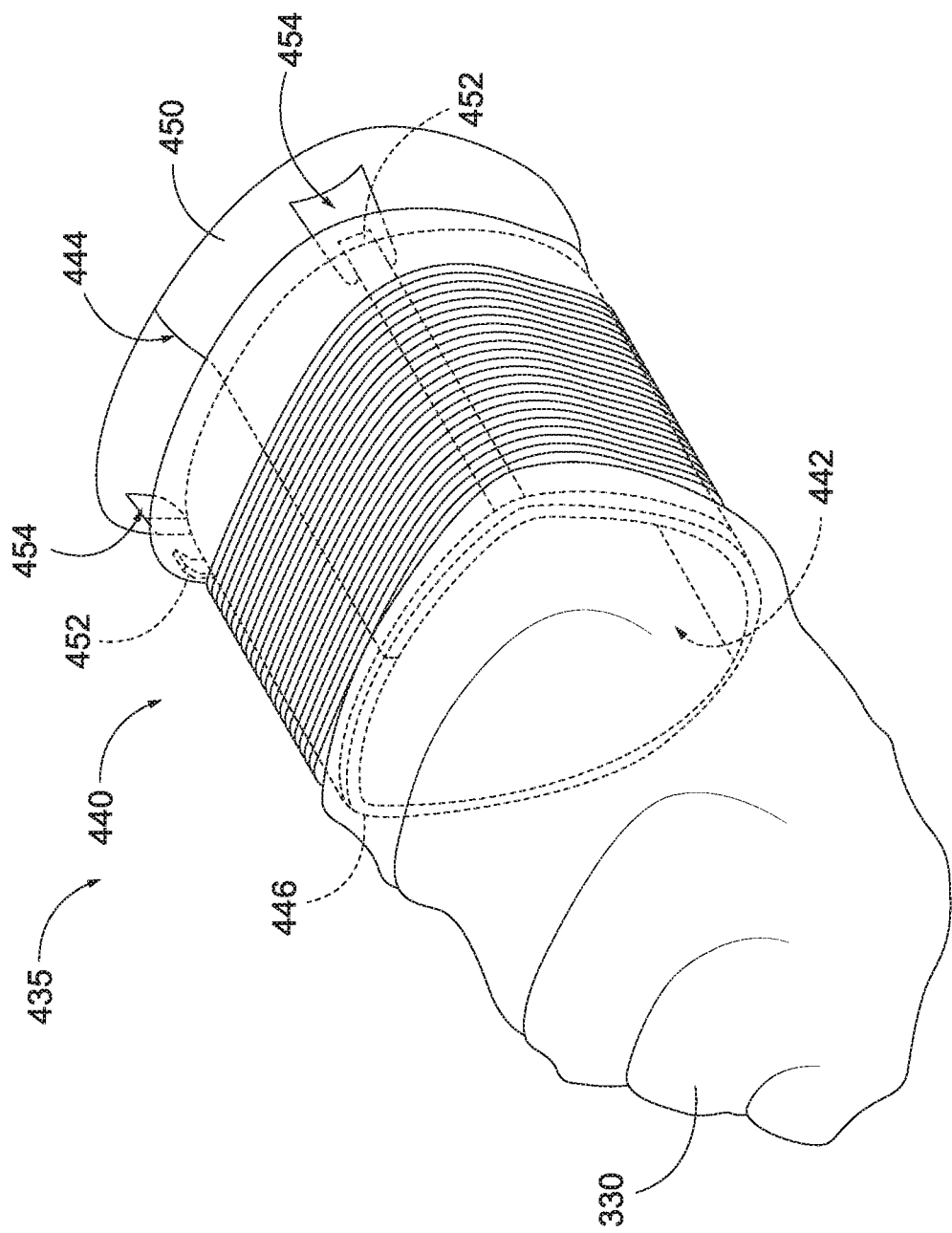
FIG. 15 depicts yet another perspective view of the sleeve ring of FIG. 11, with the flexible sterile cover secured thereto and in a compressed configuration.

FIGS. 13-15 show an exemplary use of sleeve ring (435). As seen in FIG. 13, sleeve ring (435) can be initially manipulated to flex body (440) to collapse on itself via relief slot (444). This causes one of the edges that defines relief slot (444) to fold under another edge. As a consequence, the overall size of sleeve ring (435) is reduced. This reduction in size can make it easier for an operator to stretch flexible sterile cover (330) over sheath portion (446) of body (440). Although FIG. 13 only shows a relatively small amount of flexion, it should be understood that sleeve ring (435) can be flexed any suitable amount depending on a variety of factors such as the elasticity of flexible sterile cover (330), the size and/or shape of flexible sterile cover (330), the relative strength of the operator, and/or etc. For instance, in some examples, sleeve ring (435) can be flexed until an edge defining relief slot (444) touches the opposite inflexion point or corner formed by body (440). Thus, the width of sleeve ring (435) can be reduced approximately in half in some uses. Of course, various alternative amounts of flexion can be used as will be apparent to those of ordinary skill in the art in view of the teachings herein.

Once sleeve ring (435) is flexed as desired by an operator, flexible sterile cover (330) can be slid over sheath portion (446) and into engagement with tabs (452, 458). As seen in FIG. 14, when flexible sterile cover (330) is secured onto sleeve ring (435), a portion of flexible sterile cover (330) can be manipulated to rest in the space beneath each tab (452, 458). As described above, full engagement between flexible sterile cover (330) and each tab (452, 458) is permitted by openings (454, 560), which prevent interference from horn portion (450). It should be understood that in some examples the proximal end of flexible sterile cover (330) can be rolled or can include a radial rib that can rest beneath each tab (452, 458) to provide additional support.

As also shown in FIG. 14, once flexible sterile cover (330) is secured to sleeve ring (435), body (440) can be decompressed to open relief slot (444). Once relief slot (444) is open, the resiliency of flexible sterile cover (330) causes relief slot (444) to close on itself, thereby engaging interlocking portion (445). In the present example, the triangular tongue of interlocking portion (445) engages the triangular groove of interlocking portion (445) to provide additional structural rigidity to body (440). Although this decompression step is shown as occurring after flexible sterile cover (330) is initially attached to sleeve ring (435), it should be understood that this step can be instead performed later in the procedure, as will be described in greater detail below.

As seen in FIG. 15, once flexible sterile cover (330) is initially secured to sleeve ring (435), excess length of flexible sterile cover (330) can be rolled or compressed onto the length defined by sheath portion (446). For example, the excess length can be rolled or folded onto the sleeve ring (435) in a zig-zag accordion-like manner or folded over each other. Thus, in the present use sheath portion (446) can be used to store any excess length of flexible sterile cover (330) until use of flexible sterile cover (330) is desired. As described above, this feature may be desirable in certain contexts to make the assembly of flexible sterile cover (330) and sleeve ring (435) easier to manipulate before the entire length of flexible sterile cover (330) is needed.

As also shown in FIG. 15, once flexible sterile cover (330) is rolled or compressed onto the length defined by sheath portion (446), body (440) can be decompressed to open relief slot (444). Once relief slot (444) is open, the resiliency of flexible sterile cover (330) causes relief slot (444) to close on itself, thereby engaging interlocking portion (445). As described above, this decompression procedure can be performed after flexible sterile cover (330) is initially secured to sleeve ring (435). Alternatively, this decompression procedure can be performed only after flexible sterile cover (330) is rolled or compressed onto the length defined by sheath portion (446). In some circumstances, the latter approach may be desirable to make the procedure of rolling and/or compressing flexible sterile cover (330) easier due to the decreased size of sleeve ring (435).

An operator can next insert inner retainer (310) or a combination of inner retainer (310) and holster (200) into flexible sterile cover (330) via hollow interior (442) of sleeve ring (435). Although this step can be performed regardless of whether flexible sterile cover (330) is in the unrolled position (FIG. 14) or rolled position (FIG. 15), the rolled position is generally more desirable because inner retainer (310) will not have to travel as far through flexible sterile cover (330) before reaching the distal end of flexible sterile cover (330).

Once inner retainer (310) and holster (200) are inserted into flexible sterile cover (330), external sleeve (320) can be secured to inner retainer (310) with flexible sterile cover (330) disposed between inner retainer (310) and outer retainer (320). Sleeve ring (435) can then be used to manipulate the proximal end of flexible sterile cover (330) down the length of holster cables (222). As described above, the length of flexible sterile cover (330) can generally be sized to provide approximately 2.5 feet of coverage of holster cables (222), although this length may be varied in other examples.

Figure 16:
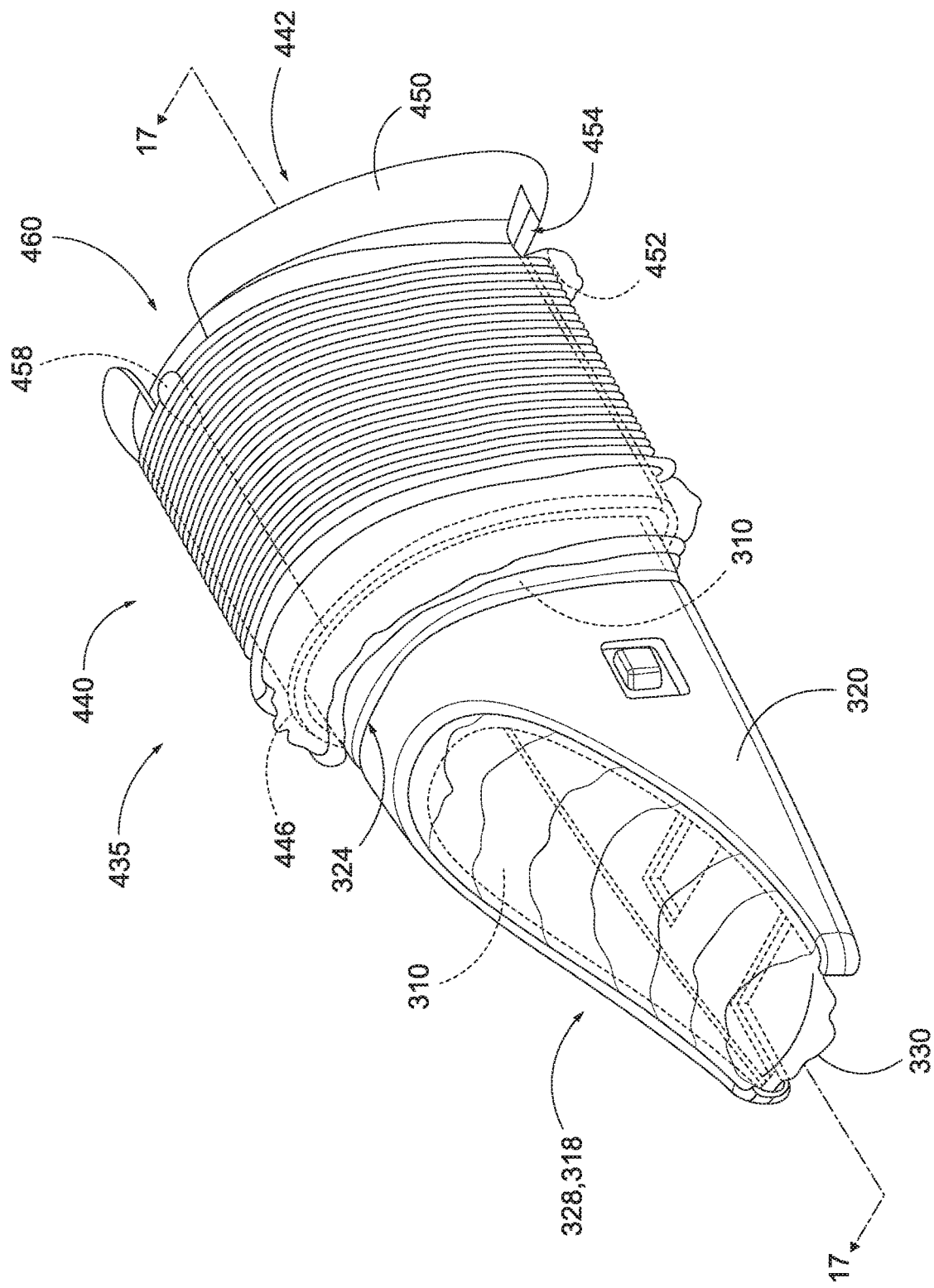
FIG. 16 depicts a perspective view of the sleeve ring of FIG. 11, with the inner and outer retainers of FIG. 2 and the flexible sterile cover of FIG. 5.
Figure 17:
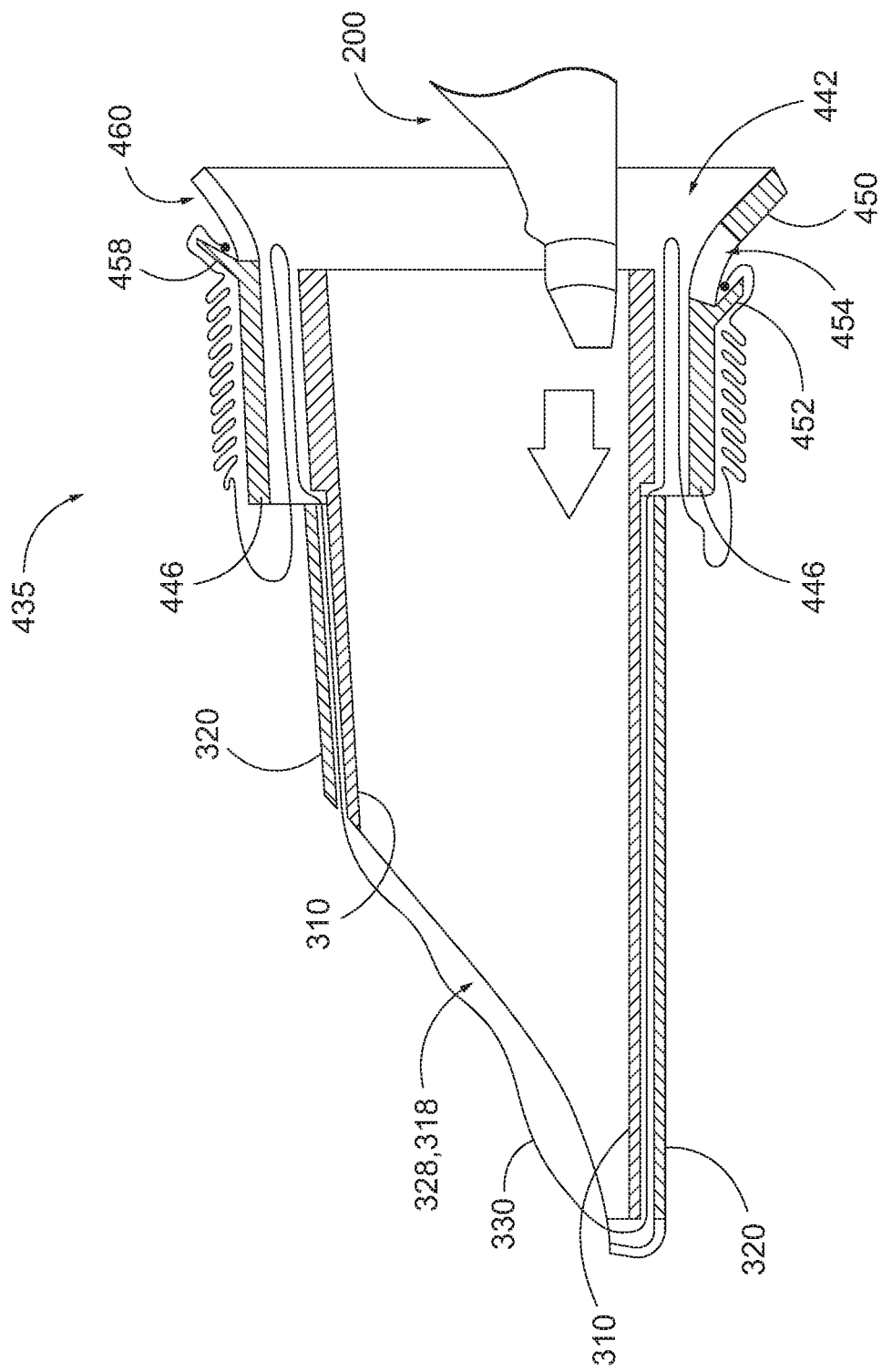
FIG. 17 depicts a side cross-sectional view of the sleeve ring of FIG. 11, with the inner and outer retainers of FIG. 2 and the flexible sterile cover of FIG. 5, the cross-section taken along line 17-17 of FIG. 16.

FIGS. 16 and 17 show a use of sleeve ring (435) with inner retainer (310), outer retainer (320), and flexible sterile cover (330). It should be understood that the state shown in FIGS. 16 and 17 corresponds to the assembly being in a shipped or packaged state. In other words, when an operator first removes the combination of sleeve ring (435), inner retainer (310), outer retainer (320), and flexible sterile cover (330) from sterile packaging, the combination can be in the state shown in FIGS. 16 and 17. As can be seen, in the packaged state, inner retainer (310) is nested within outer retainer (320). Flexible sterile cover (330) is positioned between inner retainer (310) and outer retainer (320). As can be seen, flexible sterile cover (330) is visible through top sleeve openings (318, 328). At least a portion of flexible sterile cover (330) is covered by outer retainer (320) before emerging from proximal sleeve opening (324). At this point, at least a portion of flexible sterile cover (330) can be folded distally over outer retainer (320). Flexible sterile cover (330)

then passes proximally over inner retainer (310) until reaching sleeve ring (435). At sleeve ring (435), flexible sterile cover (330) is compressed, rolled, folded, or bunched over sheath portion (446), as described above. In this configuration, the combination of sleeve ring (435), inner retainer (310), outer retainer (320), and flexible sterile cover (330) is generally configured to readily receive holster (200) with minimal manipulation and/or adjustment by an operator.

Once an operator places holster (200) within the combination of sleeve ring (435), inner retainer (310), outer retainer (320), and flexible sterile cover (330), the operator can pull sleeve ring (435) proximally away from holster (200) along holster cables (222). This can cause flexible sterile cover (330) to unroll, decompress, or otherwise extend in length as flexible sterile cover (330) is pulled off of sheath portion (446).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A biopsy device, comprising: (a) a body; (b) a needle extending from the body; and (c) a sterile cover assembly releasably coupled to the body, wherein the sterile cover assembly is configured to substantially cover the body, wherein the sterile cover assembly includes: (i) a first rigid sleeve, wherein the first rigid sleeve is configured to receive the body; (ii) a second flexible sleeve, wherein the second flexible sleeve is configured to receive the first rigid sleeve with the body contained therein; and (iii) a third rigid sleeve, wherein the third rigid sleeve is configured to receive the second flexible sleeve with the first rigid sleeve and the body contained therein.

Example 2

The biopsy device of Example 1, wherein the first rigid sleeve and the third rigid sleeve include each an interface opening, a distal opening, and a proximal opening.

Example 3

The biopsy device of Example 2, wherein the first rigid sleeve and third rigid sleeve further each include an inner channel extending between the distal opening and the proximal opening.

Example 4

The biopsy device of Example 3, wherein the inner channel of the first rigid sleeve is sized and shaped to receive the body, wherein a first length of the body is greater than a second length of the inner channel of the first rigid sleeve such that the body extends proximally from the proximal opening of the first rigid sleeve when the body is received within the inner channel of the first rigid sleeve.

Example 5

The biopsy device of Example 3, wherein the inner channel of the third rigid sleeve is sized and shaped to receive the first rigid sleeve, wherein the second length of the inner channel of the first rigid sleeve is greater than a third length of the inner channel of the third rigid sleeve such that the first rigid sleeve extends proximally from the proximal opening of the third rigid sleeve when the first rigid sleeve is received within the inner channel of the third rigid sleeve.

Example 6

The biopsy device of Example 2, wherein the interface opening of the first rigid sleeve is configured to align with the interface opening of the third rigid sleeve when the first rigid sleeve is received within the third rigid sleeve.

Example 7

The biopsy device of Example 6, wherein the interface openings of the first and third rigid sleeves are located along the first and third rigid sleeves in a position that corresponds with an interface surface of the body such that the interface surface remains operatively accessible after the body is received within the first and third rigid sleeves.

Example 8

The biopsy device of Example 5, wherein the body further includes a distal end and a proximal end, wherein the distal and proximal ends are configured to couple the body to the biopsy device.

Example 9

The biopsy device of Example 5, wherein the distal and proximal openings of the first and third rigid sleeves are configured to align with distal and proximal ends of the body to thereby allow the body to couple to a portion of the biopsy device when the body is received within the first and third rigid sleeves.

Example 10

The biopsy device of Examples 1 through 9, wherein the second flexible sleeve is formed of a latex material and has a negligible thickness.

Example 11

The biopsy device of Example 10, wherein the second flexible sleeve includes a distal closed end, a proximal open end, and a flexible inner channel.

Example 12

The biopsy device of Example 11, wherein a fourth length of the flexible inner channel is greater than the first length of the body such that the second flexible sleeve extends proximally from the proximal opening of the first rigid sleeve and the proximal end of the body when the first rigid sleeve and the body are received within the flexible inner channel of the second flexible sleeve.

Example 13

The biopsy device of Example 12, wherein the negligible thickness of the second flexible sleeve is configured to allow the distal end of the body to couple with a portion of the biopsy device when the body is received within the second flexible sleeve.

Example 14

The biopsy device of Example 13, wherein the distal closed end of the second flexible sleeve is located along the second flexible sleeve in a position that corresponds with the proximal openings of the first and third rigid sleeves and the proximal end of the body.

Example 15

The biopsy device of Example 14, wherein the negligible thickness of the second flexible sleeve is configured to allow the proximal end of the body to couple with a portion of the biopsy device when the body is received within the second flexible sleeve.

Example 16

The biopsy device of any one or more of Examples 1 through 15, further comprising a sleeve ring secured to a distal end of the second flexible sleeve, wherein the sleeve ring is configured to promote manipulation of the second flexible sleeve.

Example 17

The biopsy device of Example 16, wherein the sleeve ring includes a flange extending outwardly from the distal end of the second flexible sleeve.

Example 18

A biopsy device comprising: (a) a body; (b) a needle extending from the body; and (c) a removable cover assembly coupled to the body, wherein the removable cover assembly is configured to substantially cover the body, wherein the removable cover assembly includes: (i) an internal sleeve configured to slidably receive the body at a proximal end, wherein the body remains partially exposed on a distal end when fully received by the internal sleeve, wherein the internal sleeve includes a pair of notches; (ii) an external sleeve configured to slidably receive the internal sleeve at the proximal end, wherein the internal sleeve remains partially exposed on the distal end when fully received by the external sleeve, wherein the external sleeves include a pair of resilient latches; and wherein the pair of resilient latches are configured to releasably engage the pair of notches when the internal sleeve is slidably received within the external sleeve.

Example 19

The biopsy device of Example 18, wherein the internal sleeve and the external sleeve both include an interface opening, a distal opening, and a proximal opening.

Example 20

The biopsy device of Example 19, wherein the interface opening of the internal sleeve is configured to align with the interface opening of the external sleeve when the internal sleeve is received within the external sleeve.

Example 21

A biopsy device, comprising: (a) a body; (b) a needle extending from the body; and (c) a sterile cover assembly releasably coupled to the body, wherein the sterile cover assembly is configured to substantially cover the body, wherein the sterile cover assembly includes: (i) a first rigid sleeve, wherein the first rigid sleeve is configured to receive at least a portion of the body, (ii) a second flexible sleeve, wherein the second flexible sleeve is configured to receive the first rigid sleeve with the body contained therein, and (iii) a third rigid sleeve, wherein the third rigid sleeve is configured to receive the second flexible sleeve with the first rigid sleeve and the body contained therein.

Example 22

The biopsy device of Example 21, wherein the first rigid sleeve and the third rigid sleeve both include an interface opening, a distal opening, and a proximal opening.

Example 23

The biopsy device of Example 21, wherein the first rigid sleeve and the third rigid sleeve both include an interface opening, a distal opening, a proximal opening, and an inner channel extending between the distal opening and the proximal opening.

Example 24

The biopsy device of Example 21, wherein the first rigid sleeve and the third rigid sleeve both include an interface opening, a distal opening, a proximal opening, and an inner channel extending between the distal opening and the proximal opening, wherein the inner channel of the first rigid sleeve is sized and shaped to receive the body, wherein a first length of the body is greater than a second length of the inner channel of the first rigid sleeve such that the body extends proximally from the proximal opening of the first rigid sleeve when the body is received within the inner channel of the first rigid sleeve.

Example 25

The biopsy device of Example 21, wherein the first rigid sleeve and the third rigid sleeve both include an interface opening, a distal opening, a proximal opening, and an inner channel extending between the distal opening and the proximal opening, wherein the inner channel of the third rigid sleeve is sized and shaped to receive the first rigid sleeve, wherein a length defined by the inner channel of the first rigid sleeve is greater than a length defined by the inner channel of the third rigid sleeve such that the first rigid sleeve extends proximally from the proximal opening of the third rigid sleeve when the first rigid sleeve is received within the inner channel of the third rigid sleeve.

Example 26

The biopsy device of Example 21, wherein the first rigid sleeve and the third rigid sleeve both include an interface opening, a distal opening, and a proximal opening, wherein the interface opening of the first rigid sleeve is configured to align with the interface opening of the third rigid sleeve when the first rigid sleeve is received within the third rigid sleeve.

Example 27

The biopsy device of Example 21, wherein the first rigid sleeve and the third rigid sleeve both include an interface opening, a distal opening, and a proximal opening, wherein the interface opening of the first rigid sleeve is configured to align with the interface opening of the third rigid sleeve when the first rigid sleeve is received within the third rigid sleeve, wherein the interface openings of the first and third rigid sleeves are located along the first and third rigid sleeves in a position that corresponds with an interface surface of the body such that the interface surface remains operatively accessible after the body is received within the first and third rigid sleeves.

Example 28

The biopsy device of Example 21, wherein the body is defined by a probe and a holster, wherein the first rigid sleeve is configured to receive the holster, wherein the holster includes a distal and proximal end, wherein the distal and proximal ends of the holster are configured to couple to the probe through a portion of the second flexible sleeve.

Example 29

The biopsy device of Example 21, wherein the first rigid sleeve and the third rigid sleeve both include a distal opening, a proximal opening, and an inner channel extending between the distal opening and the proximal opening, wherein a length defined by the inner channel of the first rigid sleeve is greater than a length defined by the inner channel of the third rigid sleeve such that the first rigid sleeve extends proximally from the proximal opening of the third rigid sleeve when the first rigid sleeve is received within the inner channel of the third rigid sleeve, wherein the body is defined by a probe and a holster, wherein the first rigid sleeve is configured to receive the holster, wherein the holster includes a distal and proximal end, wherein the distal and proximal openings of the first and third rigid sleeves are configured to align with the distal and proximal ends of the holster such that the holster is configured to couple to the probe when the holster is received within the first and third rigid sleeves.

Example 30

The biopsy device of Example 21, wherein the second flexible sleeve is formed of a latex material and has a negligible thickness, wherein the second flexible sleeve includes a distal closed end, a proximal open end, and a flexible inner channel.

Example 31

The biopsy device of Example 21, wherein the second flexible sleeve includes a distal closed end, a proximal open end, and a flexible inner channel, wherein a length defined by the flexible inner channel is greater than a length defined by the body such that the second flexible sleeve extends proximally from a proximal end of the body when the first rigid sleeve and the body are received within the flexible inner channel of the second flexible sleeve.

Example 32

The biopsy device of Example 21, wherein the body is defined by a probe and a holster, wherein the first rigid sleeve is configured to receive the holster, wherein the holster includes a distal and proximal end, wherein the second flexible sleeve is formed of a latex material and has a negligible thickness, wherein the negligible thickness of the second flexible sleeve is configured to permit the distal end of the holster to couple with a portion of the probe through the second flexible sleeve.

Example 33

The biopsy device of Example 32, wherein the negligible thickness of the second flexible sleeve is configured to permit the proximal end of the holster to couple with a portion of the probe through the second flexible sleeve.

Example 34

The biopsy device of Example 21, further comprising a sleeve ring secured to a distal end of the second flexible sleeve, wherein the sleeve ring is configured to promote manipulation of the second flexible sleeve.

Example 35

The biopsy device of Example 34, wherein the sleeve ring includes a flange extending outwardly from the distal end of the second flexible sleeve.

Example 36

A biopsy device comprising: (a) a body; (b) a needle extending from the body; and (c) a removable cover assembly coupled to the body, wherein the removable cover assembly is configured to substantially cover the body, wherein the removable cover assembly includes: (i) an internal sleeve configured to receive the body at a proximal end, wherein the body remains partially exposed on a distal end when fully received by the internal sleeve, wherein the internal sleeve includes a pair of notches, and (ii) an external sleeve configured to receive the internal sleeve at the proximal end, wherein the internal sleeve remains partially exposed on the distal end when fully received by the external sleeve, wherein the external sleeves include a pair of resilient latches, wherein the pair of resilient latches are configured to releasably engage the pair of notches when the internal sleeve is received within the external sleeve.

Example 37

The biopsy device of Example 36, wherein the removable cover assembly further comprises a flexible sleeve, wherein the flexible sleeve defines a closed distal end and an open proximal end, wherein the open proximal end of the flexible sleeve is configured to receive the internal sleeve.

Example 38

The biopsy device of Example 36, wherein the removable cover assembly further comprises a flexible sleeve, wherein the flexible sleeve defines a longitudinal length, wherein the body defines a longitudinal length, wherein the longitudinal length of the flexible sleeve is greater than the longitudinal length of the body.

Example 39

The biopsy device of Example 36, wherein the removable cover assembly further comprises a flexible sleeve, wherein the flexible sleeve defines a closed distal end, an open proximal end, and a manipulator, wherein the manipulator is secured to the open proximal end, wherein the manipulator defines an opening therein configured to permit access to the open proximal end.

Example 40

A system for maintaining sterility of a biopsy device, the biopsy device including a probe and a holster, wherein the system comprises: (a) an inner cover, wherein the inner cover is configured to receive the holster of the biopsy device; (b) an outer cover, wherein the outer cover is configured to receive the inner cover, wherein the outer cover includes a fastener with the fastener being configured to removably couple the inner cover to the outer cover; and (c) a flexible sleeve, wherein the sterile cover is configured to be received between the inner cover and the outer cover, wherein the flexible sleeve defines a thickness that is configured to permit the fastener of the outer cover to engage the inner cover through a portion of the flexible sleeve.

IV. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A protective cover for use with an article, the protective cover comprising:
   a flexible cover having a closed end;
   a retainer ring configured to retain a part of the flexible cover on an outer surface of the retainer ring with the flexible cover in a folded configuration; and
   a sleeve assembly including an outer sleeve and an inner sleeve, the inner sleeve is configured to nest within the outer sleeve so as to sandwich a distal portion of the flexible cover therebetween, the retainer ring being attached to a proximal end of the flexible cover.

2. The protective cover of claim 1, the retainer ring including a body defining a slot, the slot being configured to permit a portion of the body to fold onto itself.

3. The protective cover of claim 2, the retainer ring further including an interlocking portion disposed on each side of the slot, the interlocking portion being configured to provide rigidity at the slot when each side of the slot is engaged with the other.

4. The protective cover of claim 2, the retainer ring further including an interlocking portion disposed on each side of the slot, the interlocking portion being configured to provide rigidity at the slot when each side of the slot is engaged with the other, the interlocking portion including a tongue and groove configuration.

5. The protective cover of claim 2, the body being a polymer material having a thickness configured to provide at least some flexibility.

6. The protective cover of claim 1, the retainer ring being configured to collapse onto itself to transition to a reduced diameter configuration for folding of the flexible cover onto the retainer ring.

7. The protective cover of claim 1, the retainer ring including a body, the body defining a sheath portion and a horned portion, the sheath portion retaining at least a portion of the flexible cover, the horned portion being flared outwardly relative to the sheath portion.

8. The protective cover of claim 1, the retainer ring including a body having a tab and an opening disposed adjacent to the tab, the tab and the opening being configured to releasably receive a proximal end of the flexible cover.

9. The protective cover of claim 1, the retainer ring including a body having a sheath portion, a horned portion, a tab, and an opening disposed adjacent to the tab, the tab and the opening being configured to releasably receive a proximal end of the flexible cover, the tab and the opening being positioned at an interface between the sheath portion and the horned portion.

10. The protective cover of claim 1, the flexible cover including a latex cover that has a thickness of 3 mm or less.

11. The protective cover of claim 1, the flexible cover including a distal closed end, a proximal open end, and an inner channel, a length defined by the inner channel being greater than a length defined by the retainer ring such that a portion of the flexible cover extends distally from a distal end of the retainer ring.

12. The protective cover of claim 1, further comprising a reusable holster for use with a biopsy probe, the flexible cover being configured to receive the reusable holster.

13. A protective cover for use in covering at least a portion of an article, the protective cover comprising:
a flexible cover; and
a retainer ring having a sheath portion configured to receive a portion of the flexible cover while the flexible cover is in a compressed configuration, the retainer ring defining a plurality of tabs proximate the sheath portion, each tab of the plurality of tabs being configured to engage a proximal end of the flexible cover to fasten the flexible cover to the retainer ring.

14. The protective cover of claim 13, the retainer ring being configured to flex to a collapsed position for loading of the flexible cover onto the sheath and into the compressed configuration.

15. A protective cover for use in covering at least a portion of an article, the protective cover comprising:
a flexible cover having an open end and a closed end; and
a retainer ring defining an open interior and having a sheath portion, the retainer ring being configured to move between a relaxed and a flexed configuration, the flexed configuration being configured for loading of the flexible cover onto the sheath portion, the open end of the flexible cover being configured to couple to the retainer ring for folding onto the sheath portion of the retainer ring.

16. The protective cover of claim 15, the retainer ring further defining a slot extending axially through the sheath portion, the slot being configured to permit a portion of the retainer ring to overlap with another portion of the retainer ring when the retainer ring is in the flexed configuration.

17. The protective cover of claim 15, the open end of the flexible cover being configured to receive a holster of a biopsy device.

* * * * *